US008796315B2

(12) United States Patent
McCord

(10) Patent No.: US 8,796,315 B2
(45) Date of Patent: *Aug. 5, 2014

(54) METHODS FOR IMPROVED WOUND CLOSURE EMPLOYING OLIVAMINE AND HUMAN UMBILICAL VEIN ENDOTHELIAL CELLS

(71) Applicant: Darlene E. McCord, Coralville, IA (US)

(72) Inventor: Darlene E. McCord, Coralville, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/832,188

(22) Filed: Mar. 15, 2013

(65) Prior Publication Data

US 2013/0266545 A1     Oct. 10, 2013

Related U.S. Application Data

(63) Continuation-in-part of application No. 12/823,567, filed on Jun. 25, 2010, and a continuation-in-part of application No. 12/853,908, filed on Aug. 10, 2010.

(60) Provisional application No. 61/220,485, filed on Jun. 25, 2009, provisional application No. 61/313,487, filed on Mar. 12, 2010, provisional application No. 61/235,203, filed on Aug. 19, 2009, provisional application No. 61/232,503, filed on Aug. 10, 2009.

(51) Int. Cl.
| | | |
|---|---|---|
| *A61K 31/44* | (2006.01) | |
| *A61K 31/05* | (2006.01) | |
| *A61K 31/195* | (2006.01) | |
| *A61K 31/401* | (2006.01) | |
| *A61K 31/198* | (2006.01) | |
| *A61K 31/7048* | (2006.01) | |
| *A61K 35/48* | (2006.01) | |
| *A61K 31/185* | (2006.01) | |

(52) U.S. Cl.
CPC .................. *A61K 35/51* (2013.01); *A61K 31/05* (2013.01); *A61K 31/401* (2013.01); *A61K 31/198* (2013.01); *A61K 31/7048* (2013.01); *A61K 31/185* (2013.01)
USPC ........... 514/355; 514/731; 514/561; 514/277; 514/423; 424/93.7

(58) Field of Classification Search
CPC ........... A61K 2300/00; A61K 31/4415; A61K 31/455
USPC .......... 514/355, 731, 561, 277, 423; 424/93.7
See application file for complete search history.

(56) References Cited

U.S. PATENT DOCUMENTS

| | | | |
|---|---|---|---|
| 5,733,535 | A | 3/1998 | Hollingshead et al. |
| 6,117,844 | A | 9/2000 | Fredrickson |
| 6,165,475 | A | 12/2000 | Crea et al. |
| 6,179,819 | B1 | 1/2001 | Haswell |
| 6,197,308 | B1 | 3/2001 | Crea et al. |
| 6,309,652 | B1 | 10/2001 | Aeschbach et al. |
| 6,358,542 | B2 | 3/2002 | Cuomo et al. |
| 6,416,808 | B1 | 7/2002 | Crea |
| 6,437,004 | B1 | 8/2002 | Perricone |
| 6,746,706 | B1 | 6/2004 | van der Boom et al. |
| 7,045,148 | B2 | 5/2006 | Hariri |
| 7,468,276 | B2 | 12/2008 | Hariri |
| 7,682,803 | B2 | 3/2010 | Paludan et al. |
| 7,976,836 | B2 | 7/2011 | Hariri |
| 8,034,329 | B2 | 10/2011 | Colter et al. |
| 8,105,634 | B2 | 1/2012 | Liu et al. |
| 8,202,703 | B2 | 6/2012 | Edinger et al. |
| 8,216,566 | B2 | 7/2012 | Paludan et al. |
| 8,216,599 | B2 | 7/2012 | Crea |
| 8,278,102 | B2 | 10/2012 | Ennis et al. |
| 8,293,223 | B2 | 10/2012 | Hariri |
| 8,309,070 | B2 | 11/2012 | Low et al. |
| 2003/0032179 | A1 | 2/2003 | Hariri |
| 2003/0229141 | A1 | 12/2003 | Yu et al. |
| 2004/0097428 | A1 | 5/2004 | Hamdi et al. |
| 2004/0101507 | A1 | 5/2004 | Predovan |
| 2006/0120980 | A1 | 6/2006 | Eberi |
| 2006/0121133 | A1 | 6/2006 | Chomczynski |
| 2006/0257351 | A1 | 11/2006 | Chiba |
| 2007/0053888 | A1 | 3/2007 | Hariri |
| 2007/0065396 | A1 | 3/2007 | Morariu |
| 2007/0110727 | A1 | 5/2007 | Kang |
| 2007/0178073 | A1 | 8/2007 | Chang et al. |
| 2007/0207228 | A1 | 9/2007 | Giuliani et al. |
| 2007/0298017 | A1 | 12/2007 | Han |
| 2008/0032401 | A1 | 2/2008 | Edinger et al. |
| 2008/0152629 | A1 | 6/2008 | Edinger et al. |

(Continued)

FOREIGN PATENT DOCUMENTS

| | | | |
|---|---|---|---|
| EP | 0123637 | A1 | 10/1984 |
| EP | 2070545 | A1 | 6/2009 |

(Continued)

OTHER PUBLICATIONS

Scalbert, Augustin, et al., "Absorption and metabolism of polyphenols in the gut and impact on health", Biomed Pharmacother 56 (2002), 276-282.

(Continued)

*Primary Examiner* — Shirley V Gembeh
(74) *Attorney, Agent, or Firm* — McKee, Voorhees & Sease

(57) ABSTRACT

The present disclosure relates to compositions for and methods of improving wound healing, including compositions for and methods of treating chronic wounds, and compositions for the inhibition and treatment of necrosis and extended quiescence that result in cellular necrosis instead of normal proliferation. The methods for wound healing administer one or more compositions including hydroxytyrosol and oleuropein with cells derived from umbilical cord blood.

18 Claims, 23 Drawing Sheets

(56) References Cited

U.S. PATENT DOCUMENTS

| | | |
|---|---|---|
| 2008/0226595 A1 | 9/2008 | Edinger et al. |
| 2008/0311087 A1 | 12/2008 | Gosiewska et al. |
| 2008/0311088 A1 | 12/2008 | Chang et al. |
| 2009/0053805 A1 | 2/2009 | Hariri |
| 2009/0104650 A1 | 4/2009 | Walton et al. |
| 2009/0232781 A1 | 9/2009 | Fu |
| 2009/0232782 A1 | 9/2009 | Fu |
| 2009/0280093 A1 | 11/2009 | Friedlander |
| 2010/0068194 A1 | 3/2010 | Kim |
| 2010/0113611 A1 | 5/2010 | Raederstorff et al. |
| 2010/0143289 A1 | 6/2010 | Cohen et al. |
| 2011/0217271 A1 | 9/2011 | Hariri |
| 2011/0223205 A1 | 9/2011 | Gosiewska et al. |
| 2011/0280843 A1 | 11/2011 | Edinger et al. |
| 2012/0107294 A1 | 5/2012 | Kim |
| 2012/0114712 A1 | 5/2012 | Liu et al. |
| 2012/0189583 A1 | 7/2012 | Liu et al. |
| 2012/0192873 A1 | 8/2012 | Bachmann |
| 2012/0213743 A1 | 8/2012 | Buensuceso et al. |
| 2013/0005682 A1 | 1/2013 | Raederstorff et al. |
| 2013/0039893 A1 | 2/2013 | Phan |

FOREIGN PATENT DOCUMENTS

| | | |
|---|---|---|
| JP | 2007119431 A | 5/2007 |
| WO | WO0036936 A2 | 6/2000 |
| WO | WO2004/032873 A2 | 4/2004 |
| WO | WO2006/020588 A1 | 2/2006 |
| WO | WO2008/006581 A2 | 1/2008 |
| WO | WO2008128629 A1 | 10/2008 |

OTHER PUBLICATIONS

Visioli, Fancesco, et al., "Antioxidant and Other Biological Activities of Olive Mill Waste Waters", J. Agric. Food Chem. 1999, 47, 3397-3401.

Haloui, Ehsen, et al., "Hydroxytyrosol and oleuropein from olive leaves: Potent anti-inflammatory and analgesic activities", Journal of Food, Agriculture & Environment, vol. 9 (3 & 4) (2011), 128-133.

Granados-Principal, Sergio, et al., "Hydroxytyrosol: from laboratory investigations to future clinical trials", Nutrition Reviews vol. 68 (4), 2010: 191-206.

Zhu, Lu, et al., "Hydroxytyrosol protects against oxidative damage by simultaneous activation of mitochondrial biogenesis and phase II detoxifying enzyme systems in retinal pigment epithelial cells", Journal of Nutritional Biochemistry (2010), pp. 1-10.

Zanichelli, Dario, et al., "Inhibition of *Staphylococcus aureus* by Oleuropein Is Mediated by Hydrogen Peroxide", Journal of Food Protections, vol. 68, No. 7, 2005, pp. 1492-1496.

Washington, Jennifer M., et al., "L-Proline induces differentiation of ES cells: a novel role for an amino acid in the regulation of pluripotent cells in culture", Am J Physiol Cell Physiol 298 (2010), C982-C992.

Tuck, Kellie L., et al., "Major phenolic compounds in olive oil: metabolism and health effects", Journal of Nutritional Biochemistry 13 (2002), 636-644.

Sarsour, Ehab H., et al., "Manganese Superoxide Dismutase Regulates a Metabolic Switch during the Mammalian Cell Cycle", 2012, pp. OF1-OF10.

Sarsour, Ehab H., et al., "MnSOD activity regulates hydroxytyrosol-induced extension of chronological lifespan", American Aging Association 2011, pp. 1-15.

Haber, C. Andrew, et al., "N-acetylcysteine and taurine prevent hyperglycemia-induced insulin resistance in vivo: possible role of oxidative stress", Am J Physiol Endocrinol Metab 285 (2003), E744-E753.

Victor, Victor M., et al., "N-acetylcysteine Protects Mice from Lethal Endotoxemia by Regulating the Redox State of Immune Cells", Free Radical Research, vol. 37 No. 9 (Sep. 2003), pp. 919-929.

Gonzalez-Correa, Jose Antonia, et al., "Neuroprotective effect of hydroxytyrosol and hydroxytyrosol acetate in rat brain slices subjected to hypoxia-reoxygenation", Neuroscience Letters 446 (2008), 143-146.

Vissers, Maud N., et al., "Olive Oil Phenols Are Absorbed in Humans", American Society for Nutritional Sciences, 2002, pp. 409-417.

Bisignano, Giuseppe, et al., "On the In-vitro Antimicrobial Activity of Leuropein and Hydroxytyrosol", J. Pharm. Pharmacol. 1999, 51: 971-974.

Webb, K.E., et al., "Peptide absorption: a review of current concepts and future perspectives", J Anim Sci 1992, 70: 3248-2357.

Pereira, Ana Paula, et al., "Phenolic Compounds and Antimicrobial Activity of Olive (*Olea europaea* L. Cv. Cobrancosa) Leaves", Molecules 2007, 12, 1153-1162.

Romani, Annalisa, et al., "Polyphenolic Content in Five Tuscany Cultivars of *Olea europaea* L.", J. Agric. Food Chem. 1999, 47, 964-967.

Walter, W.M., Jr., et al., "Preparation of Antimicrobial Compounds by Hydrolysis of Oleuropein from Green Olives", Applied Microbiology, Nov. 1973, vol. 26, No. 5, p. 773-776.

Capasso, Renato, et al., "Production of Glucose and Bioactive Aglycone by Chemical and Enymatic Hydrolysis of Purified Oleuropein from *Olea Europea*", Applied Biochemistry and Biotechnology, vol. 61, 1996, pp. 365-377.

Matthews, D.M., et al., "Protein absorption", J. clin. Path., 24, Suppl. (Roy. Coll. Path.), 5, 2012, pp. 29-40.

EP0123637, Soto Lucien—English Abstract.

JP2007119431, Ichimaru Pharcos—English Abstract.

Taavoni, S., et al., "Effects of olive oil on stiae gravidarum in the second trimester of pregnancy", Complementary Therapies in Clinical Practice, 2011, 167-169, 17.

PCT/US2010/040008, "International Search Report", mailed Jan. 4, 2011.

Gupta, V.J., Third party submission for U.S. Appl. No. 12/823,567, filed Jun. 25, 2010 to United States Patent and Trademark Office on Feb. 9, 2011, 19 pages.

Hengartner, M.O., "The biochemistry of apoptosis", Nature, 2000, 770-776, 407.

PCT/US2010/045049, "International Search Report", mailed Jan. 28, 2011.

Angelo, S.D., et al., "Hydroxytyrosol, a natural antioxidant from olive oil, prevents protein damage induced by long-wave ultraviolet radiation in melanoma cells", Free Radical Biology & Medicine, 2005, 908-919, 38.

Fabiani, R., et al., "Cancer chemoprevention by hydroxytyrosol isolated from virgin olive oil through G1 cell cycle arrest and apoptosis", European Journal of Cancer Prevention, 2002, 351-358, 11.

Ragione, F.D., et al., "Hydroxytyrosol, a Natural Molecule Occurring in Olive Oil, Induces Cytochrome c-Dependent Apoptosis", Biochemical and Biophysical Research Communications, 2000, 733-739, 278.

Deiana, M., et al., "Protective effect of hydroxytyrosol and its metabolite homovanillic alcohol on H2O2 induced lipid peroxidation in renal tubular epithelial cells", Food and Chemical Toxicology, 2008, 2984-2990, 46.

Fabiani, R., et al., "Inhibition of Cell Cycle Progression by Hydroxytyrosol Is Associated with Upregulation of Cyclin-Dependent Protein Kinase Inhibitors p. 21 WAF1/Cip1 and p. 27 Kip1 and with Induction of Differentiation in HL60 Cells", The Journal of Nutrition: Nutrition and Disease, 2008, 42-48.

Guichard, C., et al., "Dihydroxyphenylethanol induces apoptosis by activating serine/threonine protein phosphatase PP2A and promotes the endoplasmic reticulum stress response in human colon carcinoma cells", Carcinogenesis, 2006, 1812-1827, 27(9).

Liu, Z. et al., "Hydroxytyrosol protects retinal pigment epithelial cells from acrolein-induced oxidative stress and mitochondrial dysfunction", Journal of Neurochemistry, 2007, 2690-2700, 103.

Manna, C., et al., "Protective Effect of the Phenolic Fraction from Virgin Olive Oils against Oxidative Stress in Human Cells", Jounral of Agricultural and Food Chemistry, 2002, 6521-6526, 50.

Dog, T.L., "Menopause: a review of botanical dietary supplements", The American Journal of Medicine, 2005, 98S-108S, 118(12B).

Johnson, B.M., "In Vitro Formation of Quinoid Metabolites of the Dietary Supplement *Cimicifuga racemosa* (Black Cohosh)", Chemical Research in Toxicology, 2003, 838-846, 16(7).

(56) References Cited

OTHER PUBLICATIONS

Fernandez-Bolanos et al., "Potential use of olive by-products Extraction of interesting organic compounds from olive oil waste", Grasas y Aceites, 2006, 95-106, 57(1).
Cosenza, S.C., et al., "Evidence That the Time of Entry into S Is Determined by Events Occurring in Early G1", The Journal of Biological Chemistry, 1988, 12751-12758, 263(25).
Coller, H.A., "A New Description of Cellular Quiescence", PLos Biology, 2006, 329-349, 4.
Gray, J.V., et al., "Sleeping Beauty: in *Saccharomyces cerevisiae*", Microbiology and Molecular Biology Reviews, 2004, 187-206, 68(2).
Abu Ali Ibn-e-Sina; Al-Qaanoon-fil-Tibb, vol. II (11th century AD), Institute of History of Medicine and Medical Research, Jamia Hamdard, New Delhi-62, 1987 AD p. 213-215; pertinent portion of the listed publications and the English language translation, including the terminology conversion from the contents of Traditional Knowledge Digital Library provided by V.K. Gupta in Third Party Submission filed Feb. 9, 2011.
Abu Bakr Mohammad.Bin Zakariyya Al-Razi; Kitaab-al-Haawi-fil-Tibb,vol. III (9th century AD), Dayerah-al-Ma 'aarif Usmania, Hyderabad, (Second Edition) 1977 AD p. 321; pertinent portion of the listed publications and the English language translation, including the terminology conversion from the contents of Traditional Knowledge Digital Library provided by V.K. Gupta in Third Party Submission filed Feb. 9, 2011.
Abu Bakr Mohammad.Bin Zakariyya Al-Razi; Kitaab-al-Haawi cfil-Tibb, vol. XX (9th century AD), Dayerah-al-Ma'aarif Usmania, Hyderabad, (First Edition) 1967 AD p. 558; pertinent portion of the listed publications and the English language translation, including the terminology conversion from the contents of Traditional Knowledge Digital Library provided by V.K. Gupta in Third Party Submission filed Feb. 9, 2011.
Mohammad Azam Khan; Ikseer Azam, vol. IV (19th century AD), Matba Nizami, Kanpur, 1872 AD p. 283; pertinent portion of the listed publications and the English language translation, including the terminology conversion from the contents of Traditional Knowledge Digital Library provided by V.K. Gupta in Third Party Submission filed Feb. 9, 2011.
Ziya AJ-Din Abdullah Ibn AJ-Baitar; Al-Jaam'e-li-Mufradaat-al-Advia-w al-Aghzia; vol. IV (13th century ADI, Matba Amra, Cairo, Egypt, 1874 AD p. 105; pertinent portion of the listed publications and the English language translation, including the terminology conversion from the contents of Traditional Knowledge Digital Library provided by V.K. Gupta in Third Party Submission filed Feb. 9, 2011.
Abu Bakr Mohammad.Bin Zakariyya Al=Razi; Kitaab-al-Haawi-fil-Tibb, vol. XX (9th century ADI, Dayerah-al-Ma'aarif Usmania, Hyderabad, (First Editionl 1967 AD p. 180; pertinent portion of the listed publications and the English language translation, including the terminology conversion from the contents of Traditional Knowledge Digital Library provided by V.K. Gupta in Third Party Submission filed Feb. 9, 2011.
McCord, Darlene, PCT/US2010/045049 filed Jan. 12, 2012, "The Extended European Search Report", dated Mar. 19, 2013.

METHODS FOR IMPROVED WOUND CLOSURE EMPLOYING OLIVAMINE AND HUMAN UMBILICAL VEIN ENDOTHELIAL CELLS

CROSS-REFERENCE TO RELATED APPLICATIONS

This application is a continuation-in-part of U.S. application Ser. No. 12/823,567, filed Jun. 25, 2010, which is a non-provisional application of U.S. Provisional Application No. 61/220,485, filed Jun. 25, 2009, both titled Compositions and Methods for Wound Care, and is also a continuation-in-part of U.S. application Ser. No. 12/853,908, filed Aug. 10, 2010, which is a non-provisional application of U.S. Provisional Application Nos. 61/313,487, filed Mar. 12, 2010, 61/235,203, filed Aug. 19, 2009, and 61/232,503, filed Aug. 10, 2009, each titled Nutritional Supplements, each of which are herein incorporated by reference in their entirety.

FIELD OF THE INVENTION

The present invention generally relates to topical compositions and methods for reversing damage to skin cells and, in particular, to compositions and methods for wound healing and inhibiting necrosis. The compositions and methods may be used, for example, in the treatment of skin that is distressed or wounded as result of a disease or other biological condition or process. Beneficially, the improved methods for wound healing are provided in combination with a regenerative therapy, namely use of non-embryonic stem cells in the form of umbilical cord blood stem cells.

BACKGROUND OF THE INVENTION

The epidermis is the outermost layer of the skin and forms the protective wrap over the body's surface. The epidermis can be further subdivided into strata with the outermost layer of the epidermis being the stratum corneum which is responsible for keeping water in the body and keeping harmful chemicals and pathogens out, making skin a natural barrier to infection. Transepidermal water loss, i.e., water that passes from inside a body (animal or plant) through the epidermal layer (skin) to the surrounding atmosphere via diffusion and evaporation processes, is a normal part of the cellular activity and regulated by the stratum corneum. Excessive transepidermal water loss, however, activates an inflammatory response in the epidermis and the dermis.

Corneotherapy is a skin care concept based on repairing the stratum corneum and therefore improving the function of the skin barrier. Topically applied substances influence the biochemistry in the horny layer of the skin and subsequent processes in deeper skin layers, which consequently have effects on the constitution of the horny layer, creating a cyclical effect that starts at the surface of the skin. A healthy and functioning skin barrier provides overall protection against dehydration and the penetration of germs, allergens, irritants, radicals, and radiation. This protection supports a gradual reduction in inflammation and other skin problems as the external causative agents are repelled by an intact skin barrier.

Wound healing, or wound repair, is a process in which the skin repairs itself after injury. In normal skin, the epidermis (outermost layer) and dermis (inner or deeper layer) exists in a steady-stated equilibrium, forming a protective barrier against the external environment. Once the protective barrier is broken, the normal (physiologic) process of wound healing is immediately set in motion.

The wound healing process is susceptible to interruption or failure leading to the formation of chronic non-healing wounds, that is, a wound that does not heal in an orderly manner and in a predictable amount of time as compared to wounds resulting from surgery (also sometimes known as wounds of primary intention) or wounds caused by trauma; for example, wounds that do not heal within several months are often considered chronic. Chronic wounds present a particularly difficult problem to treat and are typically classified into three categories: venous ulcers, diabetic, and pressure ulcers. A small number of wounds that do not fall into these categories may be due to causes such as radiation poisoning or ischemia. Chronic wounds, especially ulcerative wounds such as pressure ulcers (bed sores), diabetic ulcers, venous ulcers, etc. that, without treatment, are often trapped in the inflammation phase of wound healing. These types of wounds often accelerate quickly and damage not only the skin, but underlying tissues as well. The excessive healing time required for these types of wounds can lead to secondary complications, such as permanent underlying tissue damage, nerve damage, loss of circulation, and even mortality.

Pressure ulcers and certain other chronic wounds are sometimes categorized according to severity by the use of stages. According to one protocol, Stage I is characterized by a surface reddening of the skin; to the unaided eye, the skin is unbroken and the wound is superficial. Stage II is characterized by a partial thickness skin loss involving the dermis and/or epidermis, typically presenting as an abrasion, blister (broken or unbroken), shallow crater or other lesion, that is visible to the unaided eye. Stage III wounds extend through all of the layers of the skin and are a primary site for a serious infection to occur. Stage IV wounds extend through the skin and involves underlying muscle, tendons and bone. The term "peripheral to the wound" or "peri-wound area" refers to the area adjacent to a wound (a Stage II, III or IV wound) and typically extends from immediately adjacent the wound up to about 3 to 5 cm.

There are two distinct mechanisms for cell death. Apoptosis is the result of "normal" or programmed cell death. Through this physiological process cells are routinely eliminated, giving balance to the proliferation of new cells. During apoptosis the outer membrane of the cell forms "bubbles" known as blebs. The content of the cells becomes incased in the blebs. The blebs separate from the cell and are digested by nearby cells or macrophages. This orderly process greatly reduces toxicity to surrounding cells.

Necrosis is the other form of cell death. This is not a programmed event and is known as "accidental" death. This pathological process occurs when cells are exposed to extreme stress, chemical insult, and resultant free radical damage. The early stages of necrosis involve a swelling of the cell called oncosis. During oncosis the cell and its organelles begin to swell due to an exchange in the cell's potassium to sodium ratios. Necrosis, after the oncosis stage, is an explosive event where the cells contents stream directly into the surrounding cells environment causing damage and an immune response. Controlling necrosis during the early oncosis stage is important. Up to this point, necrosis is a reversible event. The morphology of cells dying by necrosis centers on changes in the cell's permeability. Hengartner M O, The biochemistry of apoptosis. Nature 407:770-776, 2000. Osmotic changes take place during an exchange of cytosol potassium and extracellular sodium. Early stage necrosis, known as oncosis, is characterized by the dilation or swelling of the cell and its organelles due to this exchange. Cell survival of this non-programmed event is dependent upon repairing the cell's membrane and stopping the flow of sodium ions into the cells interior. Repair of the cell's membrane and improvement in the cell's environment to more homeostatic conditions are paramount to survival.

Quiescence is the counterpart to proliferation and is a normal part of the cell cycle. The cell's replicative cycle involves a myriad of molecular events that occur during the quiescent state ($G_0$) and trigger the progression to the pre-replicative ($G_1$) phase. Cosenza S C, Owen T A, Soprano D R, Soprano K J, Evidence That the Time of Entry into S is Determined by Events Occurring in Early G.sub.1. J Biological Chem. 263; 12751-12758; 1988. The $G_0$ phase represents not just the absence of signals for mitosis but an active repression of the genes needed for mitosis. This is an important distinction since cancer cells cannot enter $G_0$ and as a consequence become immortal.

During quiescence, a cell will reduce in size yet remain dynamic and metabolically active. A quiescent cell is more notable for what it doesn't do such as synthesize DNA. Coller H A, Sang L, Roberts J M, A New Description of Cellular Quiescence. PLos Biology 4:0329-0349 2006. Quiescent cells are in a "state-of-readiness," like hibernation, waiting for the appropriate signal that it is once more time to move to the G.sub.1 phase. Cells have a built-in conservation mechanism allowing it to survive for extended periods. Gray J V, Petsko G A, Johnston C, Ringe D, Singer R A, Werner-Washburne M, "Sleeping Beauty": in *Saccharomyces cerevisiae*, Microbiology and Molecular Biology Reviews 68:2; 187-206, 2004. If the cell remains in the quiescence state for an extended period, however, its ability to proliferate diminishes. Stated differently, the longer a cell stays in abnormal quiescence the more likely it becomes that the cell will die via necrosis. Just as with early stage necrosis, however, early quiescence is a reversible event that can be corrected by changing the cell's environment and reduction of free radicals in the cell's environment appears to be critical to the reversal process. See, e.g., Coller H A, Sang L, Roberts J M, A New Description of Cellular Quiescence PLoS Biol 4(3):e83.doi: 10.1371/journal.pbio.0040083 (2006).

Clinical use dating back to the late 1980's has identified umbilical cord blood as an alternative to bone marrow and peripheral blood as a source of stem cells. Recent work has involved the use of regenerative therapies for certain neurological applications, revascularization of injured tissues, and restorative wound therapies, wherein cord blood has demonstrated certain ability to regenerate various types of tissue when transplanted into animals and humans. Kim et al., Cell Transplantation, Vol. 19:1635-1644 (2010). The transplantation of human cord blood-derived endothelial progenitor cells (EPCs) has been reported to contribute to neovascularization in various ischemic diseases, leading to work involving the transplantation of cells for diabetes-impaired wound healing. However, to date such results have not been well characterized other than reports of EPCs secreting growth factors, such as keratinocyte growth factor and platelet-derived growth factor in dermal tissues. There is further evidence to suggest that paracrine factors from EPCs exert mitogenic and chemotactic effects on keratinocytes and fibroblasts to promote wound healing and increase neovascularization. Further research has identified further self-renewing capabilities of these stem cells, including documented use in neural, muscle, retinal, pancreas, skin and liver tissues.

Umbilical cord blood stem cells are an alternative to embryonic stem cells, which beneficially can be used to derive tissues from the mesodermal, endodermal and ectodermal germ lineages. Umbilical cord blood stem cells contain a mixture of different types of stem cells in prolific numbers (in comparison to other locations such as hematopoietic stem cells, endothelial stem cells, epithelial stem cells, mesenchymal stem cells and/or somatic stem cells). As a result, the documented applications of use of umbilical cord blood are reflective of the cells capability to act as multipotential cells. Harris, Stem Cell Rev. (2008) 4:269-274.

Currently, the International Cord Blood Foundation is promoting conservation and banking of cord blood. It is expected that greater awareness by physicians and expectant parents will increase the amount of retrieved cord blood. In addition, the National Institutes of Health, is also promoting research relating to the use of cord blood.

Accordingly, it is an object of the invention to provide methods for wound healing including providing a patient with a combination of Olivamine and a source of umbilical cord blood stem cells for improved treatment over conventional stem cell transplantation alone.

Accordingly, it is an objective of the claimed invention to significantly accelerate wound closure and/or promote neurovascularization of tissues, including treatment of wounds that conventionally resist healing.

A further object of the invention is to develop treatment methods for substantially decreasing time for wound repair post injury, in some aspects providing beneficial results in 12 hours post injury or even 8 hours post injury, or less.

These and other objects and aspects of the invention are set forth herein the description of the invention.

BRIEF SUMMARY OF THE INVENTION

The methods of the invention overcome a significant limitation of the art of wound healing; namely, compositions of hydroxytyrosol and oleuropein are provided with human umbilical vein endothelial cells to significantly reduce the required time for healing a wound. Although umbilical vein endothelial cells are known to provide benefits for wound healing, the methods of the present invention synergistically enhance wound repair.

In an aspect of the invention, a method for accelerating wound closure to improve wound healing is provided. In an aspect, the method includes administering or transplanting to a subject in need of wound healing a composition comprising an effective amount of hydroxytyrosol and oleuropein and an effective amount of cells derived from umbilical cord blood, wherein the administration of the composition reduces the time required for healing of the wound by at least about 30% in comparison to a composition treated with the cells derived from umbilical cord blood alone.

In a further aspect of the invention, a method for promoting cellular migration to improve wound healing is provided. In an aspect, the method includes topically administering or transplanting to a subject in need of wound healing a composition comprising hydroxytyrosol and oleuropein and cells derived from umbilical cord blood, and reducing the time required for wound healing at least 50% of a wound, as measured by cellular migration to close a wound, to below at least 12 hours.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figures 1A, 1B, 1C:
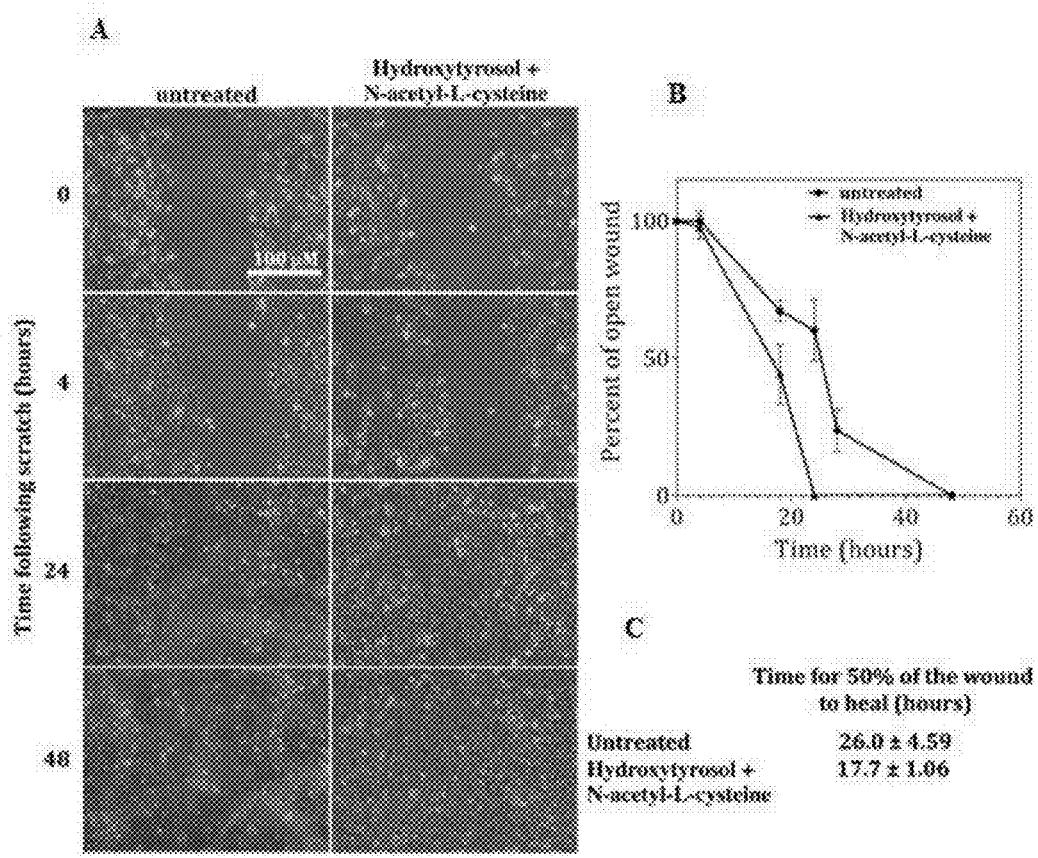
FIG. 1 shows wound healing time is decreased when treated with the present invention. (A) Comparison of wounds left untreated and treated with the present invention over 48 hours. (B) Quantification of wound healing over time either without any treatment or with treatment using the present invention. Wound healing was accelerated by treatment with the present invention at all time-points investigated. (C) Quantification of the time it takes a wound to heal by 50% in the presence or absence of treatment with the present invention. Wound healing time was synergistically improved with treatment.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE INVENTION

The embodiments of this invention are not limited to particular methods and/or compositions for treating wounds, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form. Numeric ranges recited within the specification are inclusive of the numbers defining the range and include each integer within the defined range.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

In the present invention, an "effective amount" or "therapeutically effective amount" of a compound or of a composition of the present invention is that amount of such compound and/or composition that is sufficient to effect beneficial or desired results as described herein. In terms of treatment of a mammal, e.g., a human patient, an "effective amount" is an amount sufficient to treat, reduce, manage, palliate, ameliorate, or stabilize a condition, such as a non-congenital oncosis or extended quiescence of the cells of a mammal, or both, as compared to the absence of the compound or composition.

As used herein, the term "stem cell" refers to a master cell that can reproduce indefinitely to form the specialized cells of tissues and organs. A stem cell is a developmentally pluripotent or multipotent cell. A stem cell can divide to produce two daughter stem cells, or one daughter stem cell and one progenitor ("transit") cell, which then proliferates into the tissue's mature, fully formed cells. As used herein, the term "pluripotent cell" refers to a cell that has complete differentiation versatility, i.e., the capacity to grow into any of the mammalian body's approximately 260 cell types. A pluripotent cell can be self-renewing, and can remain dormant or quiescent within a tissue. Unlike a totipotent cell (e.g., a fertilized, diploid egg cell), an embryonic stem cell cannot usually form a new blastocyst. As used herein, the term "multipotent cell" refers to a cell that has the capacity to grow into any of subset of the mammalian body's approximately 260 cell types. Unlike a pluripotent cell, a multipotent cell does not have the capacity to form all of the cell types.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

Wound Treatment

Surprisingly, it has been discovered that hydroxytyrosol, a potent anti-oxidant, can influence whether a cell is in a quiescent or proliferative state. More specifically, when present at a concentration above a threshold level, hydroxytyrosol can induce proliferative cells into a quiescent state and help maintain cells in a pre-existing quiescent state. Based upon evidence obtained to-date, the threshold concentration is about 10 μM hydroxytyrosol.

Still further, it has surprisingly been discovered that a hydroxytyrosol and oleuropein combination provides further benefits for wound healing. The combination of hydroxytyrosol and oleuropein along with additional nutritional supplement components of N-acetyl cysteine, glycine, L-taurine, L-proline and optional additional components provide further improved wound healing through the induction of proliferative cells. In addition, the administration of the hydroxytyrosol and oleuropein compositions with umbilical cord blood cells provides even further improvements in wound healing. Exemplary compositions containing hydroxytyrosol and oleuropein are commercially-available under the tradename Olivamine® (available from Pinnaclife®), such as those disclosed in related application Ser. No. 12/853,908, which is herein incorporated by reference in its entirety.

According to the invention, the delivery of cells derived from umbilical cord blood and/or transplantation of umbilical cord blood stem cells in combination with the hydroxytyrosol and oleuropein compositions provides significantly improved wound healing. As referred to herein, the use of umbilical cord blood stem cells preferably includes the use of human umbilical cord blood stem cells. The cells may also include and be referred to as umbilical vein endothelial cells (i.e. HUVEC), umbilical cord blood cells, nucleated cells derived from umbilical cord blood, or the like, which are understood to refer to cells derived from the endothelium of veins from the umbilical cord.

The umbilical cord blood stem cells according to the invention may be isolated and extracted form a healthy source, such as human cord blood and/or a cord blood source that is induced in an animal model. In some aspects, the cells are harvested from term and/or pre-term deliveries and cultured thereafter. There are various known methods of isolating these cells, including for example, a modified Ficoll-Hypaque method, a 3% gelatin method, and/or a Ficoll-Hypaque method (Kim et al., Optimal umbilical cord blood processing: Basic study for the establishment of cord blood bank, Korean Journal of Hematopoietic Stem Cell Transplantation. 2000.5: 61-68). The umbilical cord blood stem cells, in other aspects, may be obtained from commercial sources as one skilled in the art will ascertain, such as set forth in the Examples.

In still other aspects, the umbilical cord blood cells may be provided in the form of a medium conditioned by placental and/or cord blood cells. In still other aspects, the growth factors which are beneficially increased as a result of an umbilical cord blood stem cell transplant (e.g. paracrine factors) may be directly administered in place of the umbilical cord blood stem cells themselves, such as disclosed by Kim et al., Cell Transplantation, Vol. 19:1635-1644 (2010), which is herein incorporated by reference in its entirety.

According to the invention, the cells may initially be incubated and/or cultured prior to administration according to the methods of the invention. Accordingly as used herein, the cells (or the growth factors) may be transplanted, infused or otherwise provided to a mammal, such as a human, in need of wound repair. In an aspect, a composition for in vivo transplantation of cells derived from umbilical cord blood is provided for wound repair. In further aspects of the invention, a composition for in vivo transplantation of cells derived from umbilical cord blood with a composition comprising hydroxytyrosol and oleuropein is provided for wound repair.

In a preferred aspect, the umbilical vein endothelial cells are transplanted into a wound in need of treatment; thereafter the wound and transplanted cells are contacted by the compositions comprising hydroxytyrosol and oleuropein. In a preferred aspect, the hydroxytyrosol and oleuropein composition is administered in the form of a gel, hydrogel and/or solution for covering the wound and transplanted umbilical vein endothelial cells. In a still further aspect, the composition may be contacted by means of a saturated cloth or other component that covers the wound. In still other aspects, the composition may be contacted by means of direct application to the wound and transplanted cells in need of improved wound healing.

In another aspect, the wound tissue (before transplantation of the umbilical vein endothelial cells) may initially be contacted by the compositions comprising hydroxytyrosol and oleuropein. In a preferred aspect, the hydroxytyrosol and oleuropein composition is administered to the wound bed as a means of a pretreatment, such as in the form of a gel, hydrogel and/or solution for contacting the wound bed. A covering may further be applied over the treated wound bed for a period of time. Thereafter, the umbilical vein endothelial cells are transplanted into the pre-treated wound bed. According to aspects of the methods of the invention, wound repair includes the cell proliferation in a wound and/or the cellular migration toward wound healing.

According to further aspects of the methods of the invention, wound repair includes stimulated keratinocyte and/or fibroblast proliferation at an earlier time than treatments with the umbilical cord blood stem cells alone. As referred to herein, "wound repair" refers to the time required for wound closure. In some aspects according to the invention, wound repair is significantly accelerated.

In some aspects of the invention, wound repair is observed as early as 3 days post injury with the combined treatment of hydroxytyrosol and oleuropein compositions with umbilical cord blood cells. In preferred aspects, wound repair is observed as early as 1 day post injury according to the methods of the invention. In still further preferred aspects, wound repair is observed as early as 12 hours post injury, or preferably 8 hours post injury according to the methods of the invention.

Without being limited to a particular mechanism of action according to the invention, the improved and accelerated wound healing according to the methods of the invention results from the synergistic effects of the EPCs derived from the umbilical cord blood cells secreting wound healing-related growth factors, along with the beneficial effects of the hydroxytyrosol and oleuropein compositions disclosed herein. In some aspects, the wound healing-related growth factors may include for example, keratinocyte growth factor and platelet-derived growth factor in the dermal tissue where the umbilical cord blood cells are transplanted. In a further aspect, paracrine factors from EPCs may directly exert mitogenic and chemotactic effects on keratinocytes and fibroblasts to further promote wound healing and increase neovascularization of the endothelial cells of the wound.

Beneficially, according to the invention, the use of umbilical cord blood stem cells with the hydroxytyrosol and oleuropein compositions of the invention provide improved wound healing and treatment methods in comparison to use of either the Olivamine® composition and/or the EPC transplantation into a wound alone (e.g. engraftment for vasculogenesis effects). In an aspect, the combination therapy according to the invention provides at least a 25% improvement over use of an umbilical cord blood stem cell transplant alone to repair a wound. In a further aspect, the combination therapy according to the invention provides at least a 30% improvement over use of an umbilical cord blood stem cell transplant alone to repair a wound. In still further preferred aspects, the combination therapy provides at least a 50% improvement or greater, and preferably at least a 60% improvement or greater.

Clinically the improved results disclosed according to the combination therapy according to the invention result in decreased time for wound healing. In some aspects the time required for healing at least 50% of a wound (as measured by cellular migration to close a wound) was reduced below 20 hours, preferably reduced below 15 hours, preferably reduced below 10 hours, and still more preferably reduced below about 8 hours. Beneficially, the rapid repair in wound healing according to the invention results from the combined use of the hydroxytyrosol and oleuropein compositions with the umbilical cord blood stem cells allowing the synergistic results of the improvement in cellular function and the growth factor and/or cytokine action elicited by the umbilical cord blood stem cells. This is particularly beneficial in wound repair in persons having underling pathophysiological abnormalities (e.g. diabetes) wherein would repair does not following orderly progression as occurs in a healthy individual. As a result, the providing of EPCs from the umbilical cord blood stem cells is expected to overcome the reduced number of EPCs in the system of a person having such pathophysiological abnormalities.

The compositions described herein are preferably employed as topical compositions. They are preferably applied to the surface of the skin, mucosal cells and tissues (e.g., alveolar, buccal, lingual, masticatory, or nasal mucosa, and other tissues and cells that line hollow organs or body cavities) or exposed tissue.

Without being bound to any particular theory and based upon evidence obtained to-date, compositions of the present invention may be used to improve the health and viability of skin cells that are diseased or distressed as a result of a metabolic condition. For example, compositions comprising hydroxytyrosol and oleuropein may be used to reduce the concentration of free-radicals in the cells of skin tissue to improve cellular function. In addition, compositions comprising sufficient hydroxytyrosol and oleuropein may be used to induce cells into or maintain them in a reversible quiescent state to provide them with time to heal and return to a more viable state with a reduced risk of necrosis.

In a preferred embodiment, such compositions further comprise N-acetyl cysteine. In another preferred embodiment, such compositions additionally comprise N-acetyl cysteine. In another preferred embodiment, the composition further comprises hydroxytyrosol, N-acetyl cysteine and an additional component having a molecular weight not in excess of 500 Daltons that improves the health or viability of skin cells. Such additional components, for example, may be selected from the group consisting of glycine, L-taurine, L-proline, niacinamide (vitamin B3), pyridoxine (vitamin B6), methylsulfonylmethane, and combinations thereof.

The compositions and methods of the present invention may be used to treat skin that is dry, cracked, scaly, or exhibiting redness or edema but otherwise appears intact to the unaided eye. These symptoms may be presented as a result of an underlying disease or metabolic condition such as diabetes or, alternatively, may be caused by excessive transepidermal water loss. Transepidermal water loss in excess of about 5 $g/hr/cm^2$ can activate an inflammatory response in the epidermis and dermis. Many factors, such as relative humidity below 40%, changes in skin pH, normal aging and disruption of the stratum corneum contribute to excessive transepidermal water loss.

The compositions and methods of the present invention may be used to treat more serious wounds, that is, wounds characterized by a partial or total thickness skin loss, including wounds that are at risk of necrosis. When a wound is characterized by a partial or total thickness skin loss, one of the phases of wound healing is the proliferative phase. The proliferative phase typically includes angiogenesis, collagen deposition, granulation tissue formation, epithelialization, and wound contraction. Wound closure thus requires that cells be in a proliferative phase and it is preferred, therefore, that any composition applied to an open wound not induce the cells in the open wound area into a quiescent state.

According to methods of the invention wherein open wounds are treated, the use of the hydroxytyrosol and oleuropein compositions are combined with transplantation of umbilical vein endothelial cells.

In general, it is preferred that compositions applied to an open wound contain hydroxytyrosol and oleuropein in a concentration that is less than the threshold concentration at which quiescence is induced or maintained. Stated differently, it is generally preferred that compositions applied to Stage II, Stage III or Stage IV wounds contain hydroxytyrosol and oleuropein in a concentration that is less than the threshold concentration at which quiescence is induced or maintained. In one embodiment, therefore, compositions applied to an open or Stage II, III or IV wound contain hydroxytyrosol and oleuropein in a concentration not in excess of about 15 µM hydroxytyrosol and 56 µM oleuropein. For example, compositions applied to an open or Stage II, III or IV wound may contain hydroxytyrosol in a concentration of at least about 1 µM but not in excess of about 15 µM hydroxytyrosol. By way of further example, such compositions may contain hydroxytyrosol in a concentration of about 1 to about 12 µM. In certain embodiments, the concentration of hydroxytyrosol in such compositions will typically be between about 1 µM and 10 µM hydroxytyrosol. In other embodiments, the concentration of oleuropein in such compositions will typically be between about 4 µM and 60 µM oleuropein. As described herein, it is preferred that the ratio of oleuropein to hydroxytyrosol is from about 1:1 to about 10:1, preferably from about 2:1 to about 5:1, and most preferably in a ratio of about 4:1. Without being limited according to the invention all ranges within the ratios are further included within the scope of the invention.

In other regions, that is, regions appearing intact to the unaided eye such as (i) the peri-wound region surrounding an open wound, (ii) skin that is dry, cracked, scaly, or exhibiting redness or edema but otherwise appears intact to the unaided eye, or (iii) skin experiencing excessive transepidermal water loss but otherwise appears intact to the unaided eye may be treated with compositions containing hydroxytyrosol in a concentration that is greater than the concentration at which quiescence is induced or maintained. Stated differently, it is generally preferred that compositions applied to wounds not characterized by a partial or total thickness skin loss (Stage I or less severe wounds sometimes called Stage 0) contain hydroxytyrosol in a concentration that is greater than the threshold concentration at which quiescence is induced or maintained. In one embodiment, therefore, compositions applied to a Stage 0 or Stage I wound contain hydroxytyrosol in a concentration in excess of 5 µM but not in excess of about 250 µM hydroxytyrosol, and further contain oleuropein in a concentration in excess of 20 µM but not in excess of about 1000 µM oleuropein.

For example, compositions applied to (i) the peri-wound region surrounding an open wound, (ii) skin that is dry, cracked, scaly, or exhibiting redness or edema but otherwise appears intact to the unaided eye, or (iii) skin experiencing excessive transepidermal water loss but otherwise appears intact to the unaided eye may contain hydroxytyrosol in a concentration in excess of about 250 µM. In one embodiment, such compositions may contain hydroxytyrosol in a concentration of about 5 µM to about 250 µM, and an oleuropein concentration of about 20 µM to about 1000 µM. In certain embodiments, such compositions may contain hydroxytyrosol in a concentration of about 7 µM to about 225 µM, and oleuropein concentration of about 28 µM to about 900 µM. In certain embodiments, such compositions may contain hydroxytyrosol in a concentration of about 10 µM to about 200 µM, and oleuropein concentration of about 40 µM to about 800 µM. In certain embodiments, such compositions may contain hydroxytyrosol in a concentration of at least 15 µM but not in excess of 200 µM, and oleuropein concentration of at least about 60 µM but not in excess of 800 µM.

Treatment of a Stage II, III or IV wound preferably comprises treatment of the peri-wound region with a first composition and treatment of the wound region with a second composition wherein the first composition contains hydroxytyrosol in a concentration at which quiescence is induced or maintained and the second composition contains hydroxytyrosol in a concentration that is less than the concentration at which quiescence is induced or maintained. Typically, the two compositions will be applied 2 to 3 times daily at regularly spaced intervals until the wound has filled (i.e., closes); at that point, the first composition may be applied 2 to 3 times daily at regularly spaced intervals to the closed wound and the peri-wound region. Advantageously, application of the first composition to the closed wound will tend to reduce scarring. In one embodiment, the first composition will be applied to the closed wound for up to 18 months after closure of the wound without a recurrence of the wound.

Treatment of regions appearing intact to the unaided eye such as (i) the peri-wound region surrounding an open wound, (ii) skin that is dry, cracked, scaly, or exhibiting redness or edema but otherwise appearing intact to the unaided eye, or (iii) skin experiencing excessive transepidermal water loss but otherwise appearing intact to the unaided eye may be treated with compositions containing hydroxytyrosol in a concentration that is greater than the concentration at which quiescence is induced or maintained until the region is asymptomatic. For peri-wounds, the composition is preferably applied to the entire peri-wound region and adjacent skin within at least about 1 cm of the peri-wound region. Typically, the composition will be applied 2 to 3 times daily at regularly spaced intervals at least until the region is asymptomatic.

Compositions containing hydroxytyrosol in a concentration that is greater than the concentration at which quiescence is induced or maintained may also be applied prophylactically to regions that are perceived to be at risk of a chronic wound, such as venous ulcers and diabetic ulcers. In one embodiment, chronic wounds are treated using a composition of the present invention to help reverse the damage to the cells in the wound and peri-wound areas and inhibit necrosis. For example, such compositions may be applied to regions in which there are symptoms of neuropathy or lack of capillary integrity. By way of further example, such compositions may be applied to the lower leg, e.g., from the knee to the tips of the toes.

Compositions According to the Invention

In an aspect of the invention, the compositions include hydroxytyrosol or an ester or salt thereof and oleuropein. In an aspect the ratio of hydroxytyrosol to oleuropein is from about 1:1: to about 1:10, in a preferred aspect, the ratio of hydroxytyrosol to oleuropein is from about 1:2: to about 1:8, preferably about 1:4. Without being limited according to the invention all ranges within the ratios are further included within the scope of the invention.

In addition to hydroxytyrosol and oleuropein, the topical compositions of the present invention may contain N-acetyl cysteine and/or an additional component having a molecular weight not in excess of 500 Daltons that improves the health or viability of skin cells. Such additional components, for example, may include other antioxidants, vitamins, minerals, and/or amino acids. Non-limiting examples of other antioxidants include ascorbic acid (vitamin C) and its salts, ascorbyl esters of fatty acids, ascorbic acid derivatives (e.g., magnesium ascorbyl phosphate, sodium ascorbyl phosphate, and ascorbyl sorbate), EGCG, oleuropein, tocopherol (vitamin E), tocopherol sorbate, tocopherol acetate, other esters of tocopherol, tyrosol, butylated hydroxy benzoic acids and their salts, gallic acid and its alkyl esters such as propyl gallate, uric acid and its salts and alkyl esters, sorbic acid and its salts, lipoic acid, amines (e.g., N,N-diethylhydroxylamine and amino-guanidine), sulfhydryl compounds (e.g., glutathione), dihydroxy fumaric acid and it salts, glycine pidolate, arginine pilolate, nordihydroguaiaretic acid, bioflavinoids, curcumin, lyseine, methionine, proline, superoxide dismutase, resveratrol, and other polyphenols. In another embodiment, the composition comprises hydroxytyrosol, N-acetyl cysteine, and one or more of cystine, cystine derivatives, vitamin C, tannic acid, vitamin E, vitamin E derivatives, catechin, niacin, unsaturated fatty acids, vitamin P, vitamin Q, glutathione, isoflavones, guava, selenium, oleuropein or other polyphenol(s). In one embodiment, the composition comprises hydroxytyrosol, N-acetyl cysteine and one or more of glycine, L-taurine, L-proline, niacinamide (vitamin B3), pyridoxine (vitamin B6), and methylsulfonylmethane.

In one embodiment, the composition contains non-amino acid additives such as aloe vera, oat extract, hyaluronic acid, betaglucan or like substance to provide glycosaminoglycans for extracellular matrix protection. Vitamins may be additives, especially vitamins A/D3, all B vitamins and all stable C vitamins. Omega 3 and 6 fatty acids will be balanced with the greater percentage being 3. In one embodiment, the composition may contain other antioxidants, anti-inflammatory agents and tissue repair ingredients known to have wound healing benefits. For example, in one embodiment, the composition contains olive leaf extract, vitamin A/D3, Vitamin C, and essential fatty acids from olive oil, canola oil, safflower oil, borrage oil and sunflower oil. Also preferably, olive leaf extract is present in the composition of the present invention.

In one embodiment, the composition contains N-acetyl cysteine and hydroxytyrosol and the weight ratio of N-acetyl cysteine to hydroxytyrosol to between 1:1 and 50:1, respectively. In one embodiment, the composition contains N-acetyl cysteine and hydroxytyrosol and the weight ratio of N-acetyl cysteine to hydroxytyrosol is between 10:1 and 30:1, respectively. For example, in one such embodiment, the composition contains N-acetyl cysteine and hydroxytyrosol and the weight ratio of N-acetyl cysteine to hydroxytyrosol is between 20:1 and 25:1, respectively.

In one embodiment, the composition contains glycine and hydroxytyrosol and the weight ratio of glycine to hydroxytyrosol to between 1:1 and 50:1, respectively. In one embodiment, the composition contains glycine and hydroxytyrosol and the weight ratio of glycine to hydroxytyrosol is between 30:1 and 40:1, respectively. For example, in one such embodiment, the composition contains glycine and hydroxytyrosol and the weight ratio of glycine to hydroxytyrosol is about 35:1, respectively.

In one embodiment, the composition contains L-taurine and hydroxytyrosol and the weight ratio of L-taurine to hydroxytyrosol to between 1:1 and 50:1, respectively. In one embodiment, the composition contains L-taurine and hydroxytyrosol and the weight ratio of L-taurine to hydroxytyrosol is between 20:1 and 50:1, respectively. In one embodiment, the composition contains L-taurine and hydroxytyrosol and the weight ratio of L-taurine to hydroxytyrosol is between 30:1 and 40:1, respectively. For example, in one such embodiment, the composition contains L-taurine and hydroxytyrosol and the weight ratio of L-taurine to hydroxytyrosol is about 35:1, respectively.

In one embodiment, the composition contains L-proline and hydroxytyrosol and the weight ratio of L-proline to hydroxytyrosol to between 1:1 and 20:1, respectively. In one embodiment, the composition contains L-proline and hydroxytyrosol and the weight ratio of L-proline to hydroxytyrosol is between 1:1 and 10:1, respectively. In one embodiment, the composition contains L-proline and hydroxytyrosol and the weight ratio of L-proline to hydroxytyrosol is between 1:1 and 5:1, respectively.

In one embodiment, the composition contains methylsulfonylmethane and hydroxytyrosol and the weight ratio of methylsulfonylmethane to hydroxytyrosol to between 1:1 and 30:1, respectively. In one embodiment, the composition contains methylsulfonylmethane and hydroxytyrosol and the weight ratio of methylsulfonylmethane to hydroxytyrosol is between 5:1 and 25:1, respectively. In one embodiment, the composition contains methylsulfonylmethane and hydroxytyrosol and the weight ratio of methylsulfonylmethane to hydroxytyrosol is between 10:1 and 20:1, respectively.

In one embodiment, the composition contains niacinamide and hydroxytyrosol and the weight ratio of niacinamide to hydroxytyrosol to between 1:1 and 10:1, respectively. In one embodiment, the composition contains niacinamide and hydroxytyrosol and the weight ratio of niacinamide to hydroxytyrosol is between 1:1 and 5:1, respectively. In one embodiment, the composition contains niacinamide and hydroxytyrosol and the weight ratio of niacinamide to hydroxytyrosol is between 1:1 and 2:1, respectively.

In one embodiment, the composition contains pyridoxine and hydroxytyrosol and the weight ratio of pyridoxine to hydroxytyrosol to between 1:1 and 10:1, respectively. In one embodiment, the composition contains pyridoxine and hydroxytyrosol and the weight ratio of pyridoxine to hydroxytyrosol is between 1:1 and 5:1, respectively. In one embodiment, the composition contains pyridoxine and hydroxytyrosol and the weight ratio of pyridoxine to hydroxytyrosol is between 1:1 and 2:1, respectively.

In one preferred embodiment, the composition of the present invention contains hydroxytyrosol, N-acetyl cysteine and optionally one or more of glycine, L-taurine, L-proline, niacinamide (B3), pyridoxine (B6), and methylsulfonylmethane. In one example of this embodiment, the weight ratio N-acetyl cysteine to hydroxytyrosol is between 1:1 and 50:1, respectively, the weight ratio glycine to hydroxytyrosol is between 1:1 and 50:1, respectively, the weight ratio of L-taurine to hydroxytyrosol is between 1:1 and 50:1, respectively, the weight ratio of L-proline to hydroxytyrosol is between 1:1 and 20:1, respectively, the weight ratio of niacinamide to hydroxytyrosol is between 1:1 and 10:1, respectively, the weight ratio of pyridoxine to hydroxytyrosol is between 1:1 and 10:1, and the weight ratio of methylsulfonylmethane to hydroxytyrosol is between 1:1 and 30:1. In another example of this embodiment, the weight ratio N-acetyl cysteine to hydroxytyrosol is between 10:1 and 30:1, respectively, the weight ratio glycine to hydroxytyrosol is between 30:1 and 40:1, respectively, the weight ratio of L-taurine to hydroxytyrosol is between 20:1 and 50:1, respectively, the weight ratio of L-proline to hydroxytyrosol is between 1:1 and 10:1, respectively, the weight ratio of niacinamide to hydroxytyrosol is between 1:1 and 5:1, respectively, the weight ratio of pyridoxine to hydroxytyrosol is between 1:1 and 5:1, and the weight ratio of methylsulfonylmethane to hydroxytyrosol is between 10:1 and 30:1. In another example of this embodiment, the weight ratio N-acetyl cysteine to hydroxytyrosol is between 20:1 and 25:1, respectively, the weight ratio glycine to hydroxytyrosol is between 30:1 and 40:1, respectively, the weight ratio of L-taurine to hydroxytyrosol is between 30:1 and 40:1, respectively, the weight ratio of L-proline to hydroxytyrosol is between 1:1 and 5:1, respectively, the weight ratio of niacinamide to hydroxytyrosol is between 1:1 and 2:1, respectively, the weight ratio of pyridoxine to hydroxytyrosol is between 1:1 and 2:1, and the weight ratio of methylsulfonylmethane to hydroxytyrosol is between 10:1 and 20:1.

In each of the aforementioned embodiments, the components of the composition of the present invention may optionally be present in the form of an ester or a physiologically/pharmaceutically acceptable salt. Exemplary esters include the mono-, di- and triesters of hydroxytyrosol with (un)saturated carbonic acids R—COOH, whereby R is an alkyl or alkenyl chain having 2 to 22 carbon atoms. Exemplary pharmaceutically acceptable salts refer to salts prepared from pharmaceutically acceptable non-toxic acids, including inorganic salts and organic salts. Suitable non-organic salts include inorganic and organic acids such as acetic, benzene sulfonic, benzoic, camphor sulfonic, citric, ethane sulfonic, fumaric, gluconic, glutamic, hydrobromic, hydrochloric, isethionic, lactic, malic, maleic, mandelic, methanesulfonic, mucic, nitric, pamoic, pantothenic, phosphoric, succinic, sulfuric, tartaric acid, p-toluene sulfonic and other pharmaceutically acceptable salts as provided in Stahl and Wermuth "Pharmaceutical Salts Properties, Selection, and Use", 1st Ed, Wiley-VCH, 374 (2002), which is herein incorporated by reference. Thus, for example, the term "hydroxytyrosol" also encompasses pharmaceutically acceptable salts thereof such as the sodium or potassium salts, or others of the aforementioned salts, or an ester thereof.

For use in the composition of the present invention, hydroxytyrosol and oleuropein may be derived from natural sources or prepared by chemical synthesis. For example, the hydroxytyrosol and oleuropein may be obtained as an extract of, or otherwise derived from, olive leaves, olive fruits and vegetation water of olive oil production. When obtained as an extract, for example, of olive leaves, the extract will contain hydroxytyrosol, tyrosol, oleuropein, and other polyphenols. In one preferred embodiment, the hydroxytyrosol is obtained as an olive leaf extract of *Olea europaea*.

The composition may be in any form suitable for application to the body surface, and may comprise, for example, a cream, lotion, solution, suspension, emulsion, gel, ointment, paste, or the like, and/or may be prepared so as to contain liposomes, micelles, and/or microspheres. In certain embodiments, it is preferred, although not essential, that water be present. Thus, such a formulation may be aqueous, i.e., contain water, or, alternatively, may be non-aqueous. Where the formulation is non-aqueous, it may be optionally used in combination with an occlusive overlayer so that moisture evaporating from the body surface is maintained within the formulation upon application to the body surface and thereafter. In one preferred embodiment, the formulation is aqueous.

The principal differences between the physical dose forms noted above (e.g., creams, lotions, gels, and aqueous liquids) are their physical appearance and viscosity (or thickness), which are governed primarily by the presence and amount of emulsifiers and viscosity adjusters; the main ingredients are, in many cases, common among these product forms. Moreover, a particular topical formulation may often be prepared in a variety of these forms. Ointments, creams and lotions are often similar to one another, differing mainly in their viscosity (creams are typically thicker and more viscous than lotions); both lotions and creams may be opaque, translucent or clear and often contain emulsifiers, solvents (including water and alcohol) and viscosity adjusting agents. Ointments, creams and lotions also may optionally contain moisturizers and emollients, as well as fragrances, dyes/colorants, preservatives and active ingredients. Gels may be prepared with a range of viscosities, from thick (high viscosity) to thin (low viscosity) and differ principally from lotions and creams in that gels are often (but not exclusively) clear rather than opaque. Like lotions and creams, gels often contain emulsifiers, solvents (including water and alcohol) and viscosity adjusters, and may also contain moisturizers and emollients, fragrances, dyes/colorants, preservatives and active ingredients. Aqueous liquids are thinner than creams, lotions or gels, and are generally transparent; liquids usually do not contain emulsifiers. Liquid topical products often contain other solvents in addition to water (including alcohol) and may also contain viscosity adjusters, moisturizers and emollients, fragrances, dyes/colorants/pigments, preservatives and active ingredients.

Ointments, as is well known in the art of pharmaceutical formulation, are semisolid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and non-sensitizing. Ointment bases may be grouped in four classes: oleaginous bases; emulsifiable bases; emulsion bases; and water-soluble bases (see, e.g., Remington: The Science and Practice of Pharmacy, 19th Ed. (Easton, Pa.: Mack Publishing Co., 1995), pages 1399-1404). Oleaginous ointment bases include, for example, vegetable oils, fats obtained from animals, and semisolid hydrocarbons obtained from petroleum. Emulsifiable ointment bases, also known as absorbent ointment bases, typically contain little or no water and include, for example, hydroxystearin sulfate, anhydrous lanolin, and hydrophilic petrolatum. Emulsion ointment bases are generally either water-in-oil (W/O) emulsions or oil-in-water (O/W) emulsions, and include, for example, cetyl alcohol, glyceryl monostearate, lanolin, and stearic acid. Certain preferred water-soluble ointment bases are generally prepared from polyethylene glycols of varying molecular weight.

Creams, as also well known in the art, are viscous liquids or semisolid emulsions, typically either oil-in-water or water-in-oil. Cream bases are water-washable, and typically contain an aqueous phase, an oil phase, and an emulsifier. The aqueous phase (e.g., water), usually, although not necessarily, exceeds the oil phase in volume, and generally contains a humectant. The oil phase is generally comprised of petrolatum and a fatty alcohol such as cetyl or stearyl alcohol. The emulsifier in a cream formulation is generally a nonionic, anionic, cationic, or amphoteric surfactant.

Lotions are preparations to be applied to the skin surface without substantial friction, and are typically liquid or semiliquid preparations in which the active agent is present in a water or alcohol base. Lotions may also be suspensions of solids, and may comprise a liquid oily emulsion of the oil-in-water type. In certain embodiments, lotions may be preferred for treating larger body areas, because of the ease of applying a more fluid composition. Lotions will typically contain suspending agents to produce better dispersions as well as compounds useful for localizing and holding the active agent in contact with the skin, e.g., methylcellulose, sodium carboxymethylcellulose, or the like.

Gels employed in the field of pharmaceutical formulation are semisolid, suspension-type systems. Single-phase gels contain organic macromolecules distributed substantially uniformly throughout the carrier liquid, which is typically aqueous, but also, preferably, contains an alcohol and, optionally an oil. Preferred gelling agents, are cross-linked acrylic acid polymers such as the carbomer family of polymers, e.g., carboxypolyalkylenes that may be obtained commercially (e.g., Carbopol® and the like). Other exemplary hydrophilic polymers include polyethylene oxides, polyoxyethylene-polyoxypropylene copolymers, and polyvinyl alcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing, or stirring, or combinations thereof.

Pastes are semisolid dosage forms in which the active agent is suspended in a suitable base. Depending on the nature of the base, pastes may be divided between fatty pastes or those made from a single-phase aqueous gel. The base in a fatty paste is generally petrolatum, hydrophilic petrolatum, or the like. The pastes made from single-phase aqueous gels generally incorporate carboxymethylcellulose or the like as a base.

As noted above, topical formulations may also be prepared with liposomes, micelles, and microspheres. Liposomes are microscopic vesicles having a lipid wall comprising a lipid bilayer, and can be used as drug delivery systems herein as well. Generally, liposome formulations are preferred for poorly soluble or insoluble pharmaceutical agents. Liposomal preparations may include cationic (positively charged), anionic (negatively charged), and neutral preparations. Cationic liposomes are readily available and include, for example, N[1-2,3-dioleyloxy)propyl]-N,N,N-triethylammonium (DOTMA) liposomes are available under the tradename Lipofectin® (GIBCO BRL, Grand Island, N.Y.). Similarly, anionic and neutral liposomes are readily available as well, e.g., from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), and dioleoylphosphatidyl ethanolamine (DOPE), among others. These materials can also be mixed with DOTMA in appropriate ratios. Methods for making liposomes using these materials are well known in the art.

Micelles are known in the art as comprised of surfactant molecules arranged so that their polar headgroups form an outer spherical shell, while their hydrophobic, hydrocarbon chains are oriented towards the center of the sphere, forming a core. Micelles form in an aqueous solution containing surfactant at a high enough concentration so that micelles naturally result. Surfactants useful for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethylammonium chloride, dodecylammonium chloride, polyoxyl 8 dodecyl ether, polyoxyl 12 dodecyl ether, nonoxynol 10, and nonoxynol 30. Micelle formulations can be used in conjunction with the present disclosure either by incorporation into the reservoir of a topical or transdermal delivery system, or into a formulation to be applied to the body surface.

Microspheres, similarly, may be incorporated into the present topical formulations and drug delivery systems. Like liposomes and micelles, microspheres essentially encapsulate a drug or drug-containing formulation. Microspheres are generally, although not necessarily, formed from synthetic or naturally occurring biocompatible polymers, but may also be comprised of charged lipids such as phospholipids. Preparation of microspheres is well known in the art and described in the pertinent texts and literature.

The choice of a particular formulation carrier or vehicle will depend on the particular physical form and mode of delivery that the formulation is to achieve. Suitable topical vehicles and vehicle components for use with the formulations described herein (including, for example, the physical dose forms discussed above) are well known in the cosmetic and pharmaceutical arts, and include such vehicles (or vehicle components) and carriers as water; organic solvents such as alcohols (particularly lower alcohols readily capable of evaporating from the skin such as ethanol), glycols (such as propylene glycol, butylene glycol, and glycerin), aliphatic alcohols (such as lanolin); mixtures of water and organic solvents (such as water and alcohol), and mixtures of organic solvents such as alcohol and glycerin (optionally also with water); lipid-based materials such as fatty acids, acylglycerols (including oils, such as mineral oil, and fats of natural or synthetic origin), phosphoglycerides, sphingolipids and waxes; protein-based materials such as collagen and gelatin; silicone-based materials (both non-volatile and volatile) such as cyclomethicone, demethiconol and dimethicone copolyol (Dow Corning); hydrocarbon-based materials such as petrolatum and squalane; anionic, cationic and amphoteric surfactants and soaps; sustained-release vehicles such as microsponges and polymer matrices; stabilizing and suspending agents; emulsifying agents; and other vehicles and vehicle components that are suitable for administration to the skin, as well as mixtures of topical vehicle components as identified above or otherwise known to the art. In one particular embodiment, the carrier or vehicle comprises water. The vehicle may further include components adapted to improve the stability or effectiveness of the applied formulation, such as preservatives, antioxidants, skin penetration enhancers, sustained release materials, and the like. Examples of such vehicles and vehicle components are well known in the art and are described in such reference works as Martindale—The Extra Pharmacopoeia (Pharmaceutical Press, London 1993) and Remington's Pharmaceutical Sciences.

In certain embodiments, the formulation includes a solvent. Suitable solvents for use in the formulations of the present invention include, but are not limited to, water, ethanol, butylene glycol, propylene glycol, isopropyl alcohol, isoprene glycol, glycerin, Carbowax 200, Carbowax 400, Carbowax 600, and Carbowax 800. In addition, combinations or mixtures of these solvents may be used according to the present invention. In one particular embodiment, the solvent is water.

Depending on the particular physical dose form, an emulsifier may be included. Suitable emulsifiers for use in the formulations described herein include, but are not limited to, Incroquat Behenyl TMS (behentrimonium methosulfate, cetearyl alcohol), non-ionic emulsifiers like polyoxyethylene oleyl ether, PEG-40 stearate, ceteareth-12 (e.g., Eumulgin B-1 manufactured by Henkel), ceteareth-20 (e.g., Eumulgin B-2 manufactured by Henkel), ceteareth-30, Lanette O (manufactured by Henkel; ceteareth alcohol), glyceryl stearate (e.g., Cutina GMS manufactured by Henkel), PEG-100 stearate, Arlacel 165 (glyceryl stearate and PEG-100 stearate), steareth-2 and steareth-20, or combinations/mixtures thereof, as well as cationic emulsifiers like stearamidopropyl dimethylamine and behentrimonium methosulfate, or combinations/mixtures thereof. In addition, cationic emulsifiers may be combined or mixed with non-ionic emulsifiers.

Suitable viscosity adjusting agents (i.e., thickening and thinning agents) for the formulations described herein include, but are not limited to, protective colloids or non-ionic gums such as hydroxyethylcellulose (e.g., Cellosize HEC QP52,000-H, manufactured by Amerchol), xanthan gum, and sclerotium gum (Amigel 1.0), as well as magnesium aluminum silicate (Veegum Ultra), silica, microcrystalline wax, beeswax, paraffin, and cetyl palmitate. In addition, appropriate combinations or mixtures of these viscosity adjusters may be utilized.

Suitable surfactants for use in the formulations of the present invention include, but are not limited to, nonionic surfactants like Surfactant 190 (dimethicone copolyol), Polysorbate 20 (Tween 20), Polysorbate 40 (Tween 40), Polysorbate 60 (Tween 60), Polysorbate 80 (Tween 80), lauramide DEA, cocamide DEA, and cocamide MEA, amphoteric surfactants like oleyl betaine and cocamidopropyl betaine (Velvetex BK-35), and cationic surfactants like Phospholipid PTC (Cocamidopropyl phosphatidyl PG-dimonium chloride). Combinations of surfactants may also be employed.

The formulations may also include one or more preservatives. Suitable preservatives include, but are not limited to, anti-microbials such as Germaben II (manufactured by ICI; propylene glycol, diazolidinyl urea, methylparaben, and propylparaben), methylparaben, propylparaben, imidazolidinyl urea, benzyl alcohol, sorbic acid, benzoic acid, sodium benzoate, dichlorobenzyl alcohol, and formaldehyde, as well as physical stabilizers and anti-oxidants such as alpha-tocopherol (vitamin E), sodium ascorbate/ascorbic acid, ascorbyl palmitate and propyl gallate. In addition, combinations or mixtures of these preservatives may also be used.

Various additives, known to those skilled in the art, may also be included in the topical formulations. In certain embodiments, for example, it may be desirable to include one or more skin permeation enhancers in the formulation. Examples of suitable enhancers include, but are not limited to, ethers such as diethylene glycol monoethyl ether (available commercially as Transcutol®) and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80), and lecithin (U.S. Pat. No. 4,783,450); alcohols such as ethanol, propanol, octanol, benzyl alcohol, and the like; polyethylene glycol and esters thereof such as polyethylene glycol monolaurate (PEGML; see, e.g., U.S. Pat. No. 4,568,343); amides and other nitrogenous compounds such as urea, dimethylacetamide (DMA), dimethylformamide (DMF), 2-pyrrolidone, 1-methyl-2-pyrrolidone, ethanolamine, diethanolamine, and triethanolamine; terpenes; alkanones; and organic acids, particularly citric acid and succinic acid. Azone® and sulfoxides such as DMSO and C10 MSO may also be used.

Other enhancers are those lipophilic co-enhancers typically referred to as "plasticizing" enhancers, i.e., enhancers that have a molecular weight in the range of about 150 to 1000, and an aqueous solubility of less than about 1 wt. %. Lipophilic enhancers include fatty esters, fatty alcohols, and fatty ethers. Examples of specific fatty acid esters include methyl laurate, ethyl oleate, propylene glycol monolaurate, propylene glycerol dilaurate, glycerol monolaurate, glycerol monooleate, isopropyl n-decanoate, and octyldodecyl myristate. Fatty alcohols include, for example, stearyl alcohol and oleyl alcohol, while fatty ethers include compounds wherein a diol or triol, e.g., a C2-C4 alkane diol or triol, is substituted with one or two fatty ether substituents.

Additional permeation enhancers will be known to those of ordinary skill in the art of topical drug delivery, and/or are described in the pertinent texts and literature. See, e.g., Percutaneous Penetration Enhancers, eds. Smith et al. (CRC Press, 1995).

The formulations may also comprise one or more moisturizers. Suitable moisturizers for use in the formulations of the present disclosure include, but are not limited to, lactic acid and other hydroxy acids and their salts, glycerin, propylene glycol, butylene glycol, sodium PCA, Carbowax 200, Carbowax 400, and Carbowax 800. Suitable emollients for use in the formulations described herein include, but are not limited to, PPG-15 stearyl ether, lanolin alcohol, lanolin, lanolin derivatives, cholesterol, petrolatum, isostearyl neopentanoate, octyl stearate, mineral oil, isocetyl stearate, Ceraphyl 424 (myristyl myristate), octyl dodecanol, dimethicone (Dow Corning 200-100 cps), phenyl trimethicone (Dow Corning 556), Dow Corning 1401 (cyclomethicone and dimethiconol), and cyclomethicone (Dow Corning 344), and Miglyol 840 (manufactured by Huls; propylene glycol dicaprylate/dicaprate). In addition, appropriate combinations and mixtures of any of these moisturizing agents and emollients may be used in accordance with the present invention.

Suitable fragrances and colors, such as FD&C Red No. 40 and FD&C Yellow No. 5, may also be used in the formulations. Other examples of fragrances and colors suitable for use in topical products are known in the art.

Other suitable additional and adjunct ingredients which may be included in the formulations of the present invention include, but are not limited to, abrasives, absorbents, anti-caking agents, anti-foaming agents, anti-static agents, astringents (e.g., witch hazel, alcohol, and herbal extracts such as chamomile extract), binders/excipients, buffering agents, chelating agents (e.g., Versene EDTA), film forming agents, conditioning agents, opacifying agents, pH adjusters (e.g., citric acid and sodium hydroxide), and protectants. Examples of each of these ingredients, as well as examples of other suitable ingredients in topical product formulations, may be found in publications by The Cosmetic, Toiletry, and Fragrance Association (CTFA). See, e.g., CTFA Cosmetic Ingredient Handbook, 2nd edition, eds. John A. Wenninger and G. N. McEwen, Jr. (CTFA, 1992).

The formulations may also contain irritation-mitigating additives to minimize or eliminate the possibility of skin irritation or skin damage resulting from the pharmacologically active base or other components of the composition. Suitable irritation-mitigating additives include, for example: alpha-tocopherol; monoamine oxidase inhibitors, particularly phenyl alcohols such as 2-phenyl-1-ethanol; glycerin; salicylic acids and salicylates; ascorbic acids and ascorbates; ionophores such as monensin; amphiphilic amines; ammonium chloride; N acetyl cysteine; cis-urocanic acid; capsaicin; and chloroquine. The irritant-mitigating additive, if present, may be incorporated into the present formulations at a concentration effective to mitigate irritation or skin damage.

Administration of Compositions for Wound Healing

The compositions and formulations described herein can be administered as a pre-treatment (e.g. prior to a wound) such that cells are pretreated with the hydroxytyrosol and oleuropein prior to an injury or wound. In other embodiments, the compositions and formulations described herein are administered with the umbilical cord blood stem cells as a treatment to an existing wound.

The compositions and formulations described herein can be administered in accordance with a number of topical delivery routes and/or mechanisms. The method of delivery of the compositions may vary, but generally involves application of a formulation comprising hydroxytyrosol to an area of body surface affected with a wound, or the area surrounding such wound (i.e., the peri wound). For example, in one embodiment gels may be preferred for areas in which there is a partial or total loss of skin layers (Stage II, III or IV wounds) and ointments will be prepared for areas in which the skin appears to be intact to the unaided eye. Typical modes of delivery include application using the fingers; application using a physical applicator such as a cloth, tissue, swab, stick or brush (as achieved for example by soaking the applicator with the formulation just prior to application, or by applying or adhering a prepared applicator already containing the formulation—such as a treated or premoistened bandage, wipe, washcloth or stick—to the skin); spraying (including mist, aerosol or foam spraying); dropper application (as for example with ear drops); sprinkling (as with a suitable powder form of the formulation); and soaking A gel, cream, ointment, or lotion, for example, may be spread on the affected surface and optionally gently rubbed in. A solution may be applied in like manner, but more typically will be applied with a dropper, swab, or the like, and carefully applied to the affected areas. Solutions may also be sprayed onto a surface using a spray applicator; being mixed with fibrin glue and applied (e.g., sprayed) onto a surface. In some embodiments, a composition of the present invention may be impregnated into absorptive materials, such as dressings, bandages, patches, and gauze, or coated onto the surface of solid phase materials, and placed on an affected area, with or without the use of gentle pressure and/or an adhesive material to secure the material to the area.

Other types and configurations of topically applied drug delivery systems may also be used in conjunction with the present invention, as will be appreciated by those skilled in the art of transdermal drug delivery. See, for example, Ghosh, Transdermal and Topical Drug Delivery Systems (Interpharm Press, 1997), particularly Chapters 2 and 8.

The dose regimen will depend on a number of factors that may readily be determined, such as severity of the affected region and responsiveness of the condition to be treated, but will normally be one or more doses per day, with a course of treatment lasting from several days to several months, or until a cure is effected or a diminution of disease state is achieved. One of ordinary skill may readily determine optimum dosages, dosing methodologies, and repetition rates. In general, it is contemplated that the formulation will be applied one to four times daily. With a skin patch, bandage, or dressing, the device is generally maintained in place on the body surface throughout a drug delivery period, typically in the range of 8 to 72 hours, and replaced as necessary.

The method of promoting cell health of the cells of a mammal is useful for, among other things, the treatment or prevention of skin ailments. Treatment of lymphedema-induced pruritis and of ichthyosis with an effective amount of the composition of the present invention is shown to treat or palliate the skin manifestations occurring in these disorders. Topical formulations were effective upon following the treatment regimen.

Without seeking to limit the invention or to be bound by any particular theory, it is believed that promoting or maintaining cell health of the cells of a mammal by administering a therapeutically effective amount of a composition of the present invention may act through one or more of the following mechanisms: a) treating or preventing oncosis or extended quiescence of the cells; b) maintaining or increasing the amount of adenosine triphosphate (ATP) in the extracellular spaces within a mammal; c) repairing the cell membranes within a mammal; d) restoring the normal osmotic balance across the cell membranes or stopping the flow of sodium ions in the cells; e) activating quiescent cells that have not moved normally through the cell cycle; f) protecting against free radical damage to the cell, its organelles and the extracellular spaces; and g) protecting against cellular necrosis during the pre-lethal stages.

Having described the invention in detail, it will be apparent that modifications and variations are possible without departing the scope of the invention defined in the appended claims.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. The contents of all references, patents, and patent applications cited throughout this application are hereby incorporated by reference. The invention is further illustrated by the following examples, which should not be construed as further limiting.

All publications and patent applications in this specification are indicative of the level of ordinary skill in the art to which this invention pertains. All publications and patent applications are herein incorporated by reference to the same extent as if each individual publication or patent application was specifically and individually indicated by reference.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

Figure 2:
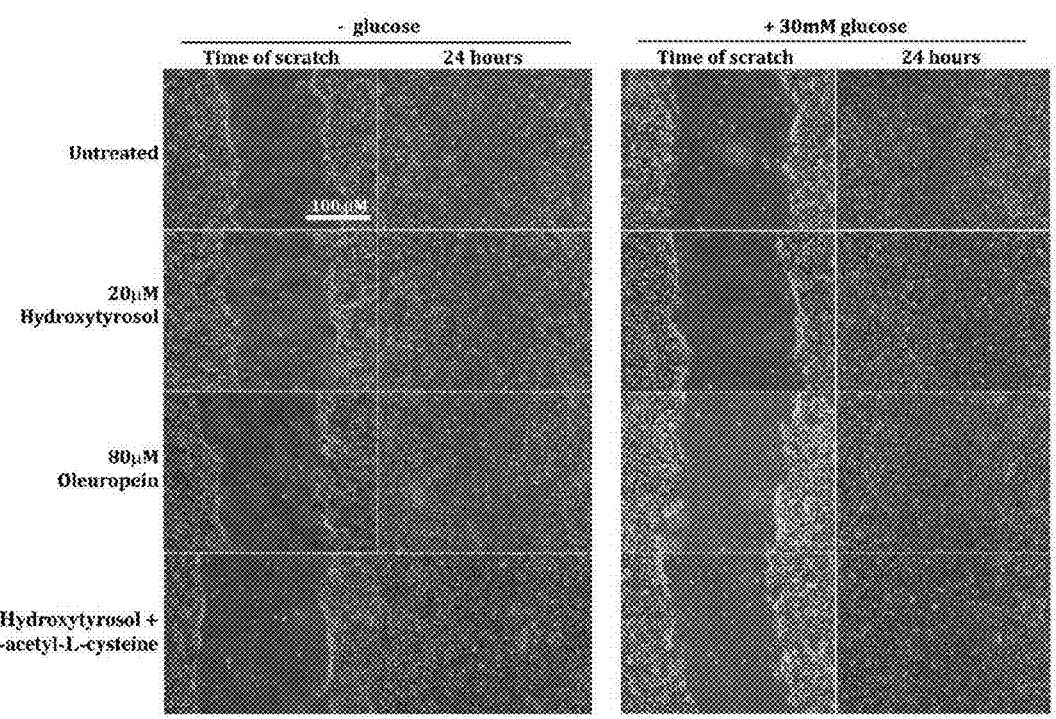
FIG. 2 shows compositions according to the invention improve wound healing both in the presence and absence of glucose.
Figure 3:
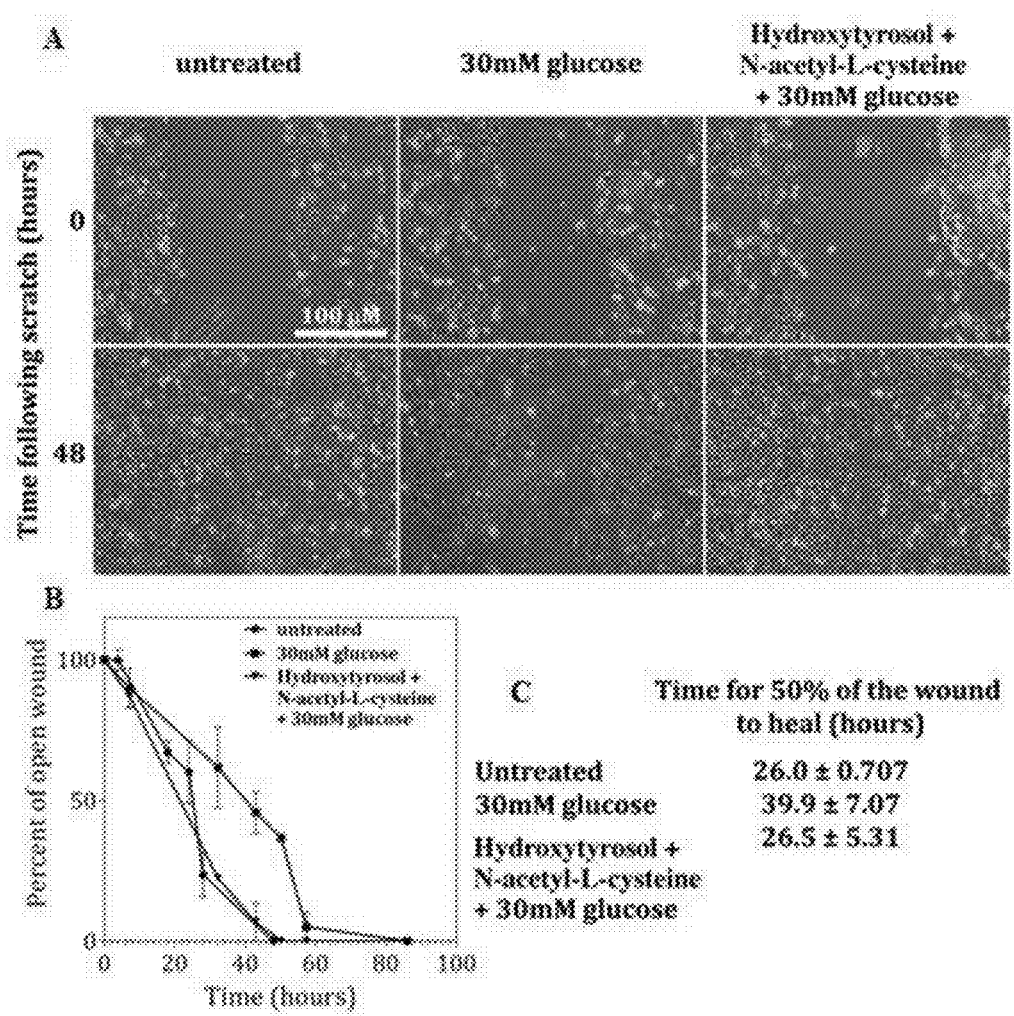
FIG. 3 shows impaired wound healing in the presence of high glucose concentrations is normalized by treatment with the composition of the present invention. (A) Comparison of wound healing in the presence of the combination of hydroxytyrosol and N-acetyl-L-cysteine of the present invention with high glucose (HT+NALC+glucose), in the presence of high glucose alone, or untreated. (B) Quantification of wound healing in panel A. The HT+NALC combination maintains healthy wound healing times in a high glucose environment (C) Comparison of the three treatments for the time it takes the wound to heal by 50%.

Original wound healing data evaluated the use of hydroxytyrosol and N-acetyl-L-cysteine for endothelial cell survival by 50%, and that in the presence of glucose, normal healing rates could be maintained by the combination. FIGS. 1-3 and Table 1 show the combination of hydroxytyrosol and N-acetyl-L-cysteine produced a synergistic effect on the time and extent of wound healing, both in the absence of glucose, and in the presence of glucose. The time for half of a wound to heal was shorter when both hydroxytyrosol and N-acetyl-cysteine were present than the additive effect of the compounds; N-acetyl-cysteine by itself increased the time to 50% healing compared to untreated. This is extremely significant and unexpected, primarily in light of the Warburg Effect, whereby high glucose levels impair wound healing.

TABLE 1

| Treatment | Time for 50% wound to heal (hours) | SD |
|---|---|---|
| Untreated | 26.01 | 0.71 |
| Present Art | 17.75 | 1.06 |
| Hydroxytyrosol | 19.25 | 1.84 |
| Oleuropein | 25.62 | 2.17 |
| N-acetylcysteine | 28.87 | 1.95 |

As shown in Table 1, hydroxytyrosol and N-acetyl-L-cysteine work synergistically in wound healing. The time for wounds to heal by 50% under the various treatment conditions was quantified. Present Art is the combination of hydroxytyrosol and N-acetyl-L-cysteine of certain embodiments disclosed herein. The combination of hydroxytyrosol and N-acetyl-L-cysteine reduced healing times seen for each ingredient individually by up to 50%.

Figure 4:
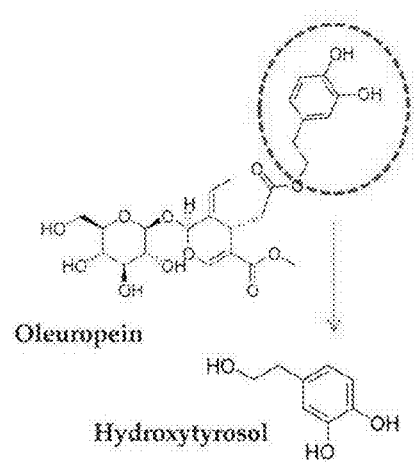
FIG. 4 shows the hydrolysis of oleuropein (25% is composed of hydroxytyrosol) into hydroxytyrosol.

Additional research was conducted to demonstrate that the combination of hydroxytyrosol and N-acetyl-L-cysteine improves cell migration in an in vitro model of wound healing in human microvascular endothelial cells and improves wound healing by 50% as compared to untreated cells. In addition, oleuropein, of which 25% is composed of hydroxytyrosol and which is hydrolyzed into hydroxytyrosol (see FIG. 4), does not improve wound healing, and hydroxytyrosol alone is 30% less effective than when dosed at the concentrations anticipated by the present art (Table 1). Thus, the polyphenol oleuropein further including hydroxytyrosol allows for new treatment possibilities according to the embodiments of the invention.

Figure 5:
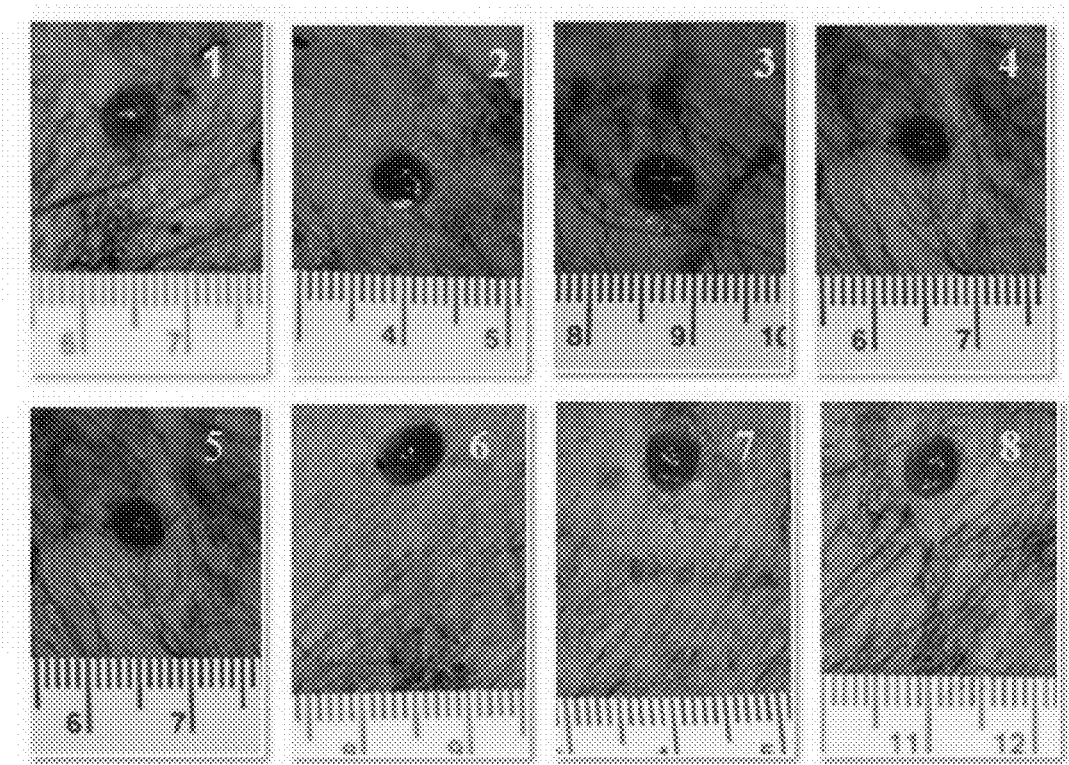
FIG. 5 shows various photographs of a 7 day wound blind study of wound healing using a combination of hydroxytyrosol and N-acetyl-L-cysteine, wherein wound No. 2 shows significantly better wound healing than other wound sites.

This is demonstrated in FIG. 5 wherein treatments using the combination of hydroxytyrosol and N-acetyl-L-cysteine were provided topically in vivo. As shown in FIG. 5, wounds inflicted on a subject heal better when treated with the combination of hydroxytyrosol and N-acetyl-L-cysteine of the present invention.

Without being limited to a mechanism of the invention, the in vivo research has uncovered a heretofore unknown pathway that causes the cell to convert from anaerobic metabolism to aerobic energy production. The prior art did not contemplate the unique epigenetic interactions and mechanisms of olive phenolic compounds with the genome and the unique epigenetic interactions and mechanisms of olive phenolic compounds with the genome.

Example 2

Additional wound studies were conducted using umbilical cord stem cells in addition to the use of hydroxytyrosol compositions and commercially-available Olivamine® compositions (20 µM hydroxytyrosol, 80 µM oleuropein, 2 mM N-acetylcysteine, 50 µM L-proline, 2 mM glycine and 100 µM taurine). These were evaluated with human umbilical vein endothelial cells (HUVEC) to assess impact on cell migration and wound healing.

HUVEC cells. Human umbilical vein endothelial cells are derived from the endothelium of veins from the umbilical cord (HUVEC primary cells purchased from Lonza). HUVECs have been widely used as a model system for the study of the regulation of endothelial cell function and the role of the endothelium in response of the blood vessel wall to stretch, shear forces and the development of atherosclerotic plaques and angiogenesis. For the following study, HUVECs are a primary endothelial cell line as a model system for the function and pathology of endothelial cells. We investigated improvement in cell proliferation and migration following treatment with Olivamine.

In this study, HUVEC cells were pre-treated with or without 30 mM glucose for 3 days (72 hours). The cells were then equilibrated for a day (24 hours), and incubated with 50 µM hydroxytyrosol or Olivamine formulation (20 µM hydroxytyrosol, 80 µM oleuropein, 2 mM N-acetylcysteine, 50 µM L-proline, 2 mM glycine and 100 µM taurine) for 24 hours before wounding.

Figure 6A:
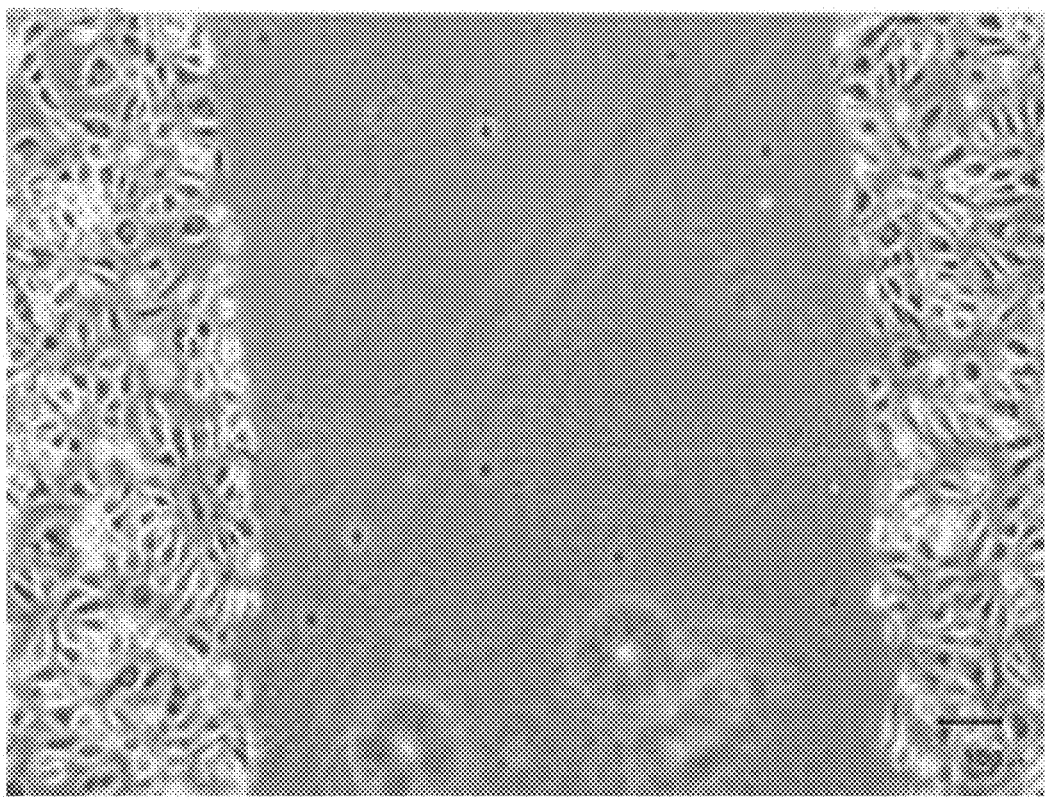
FIGS. 6A-6B show exemplary images of measurements of the distance between wound openings at varying points of time, pursuant to Example 2 of the application.
Figure 6B:
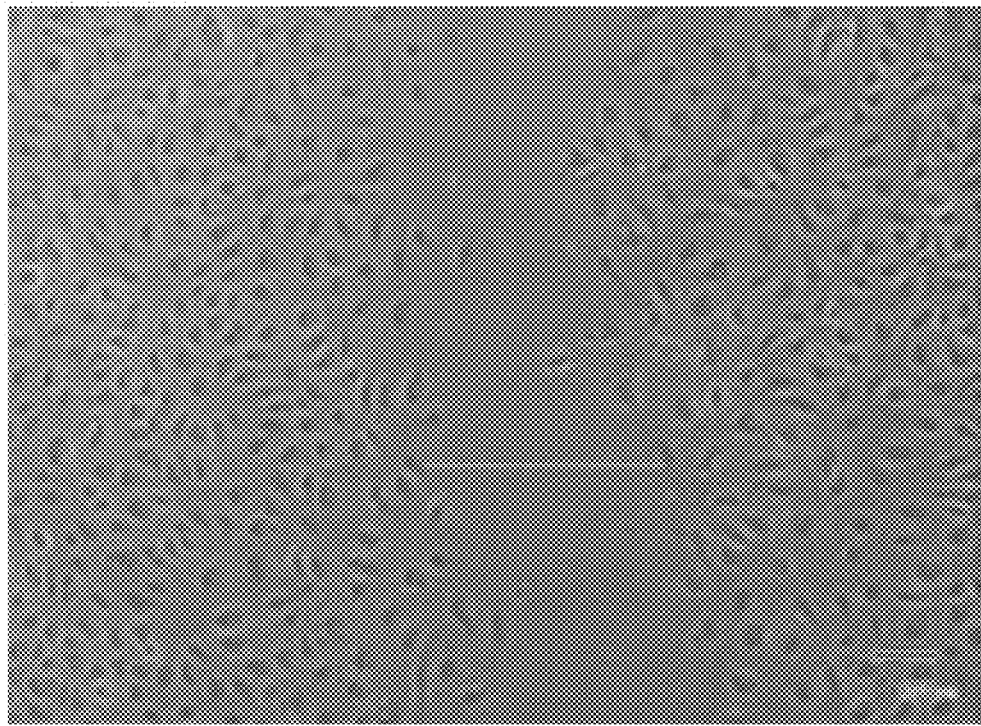
Figure 7A:
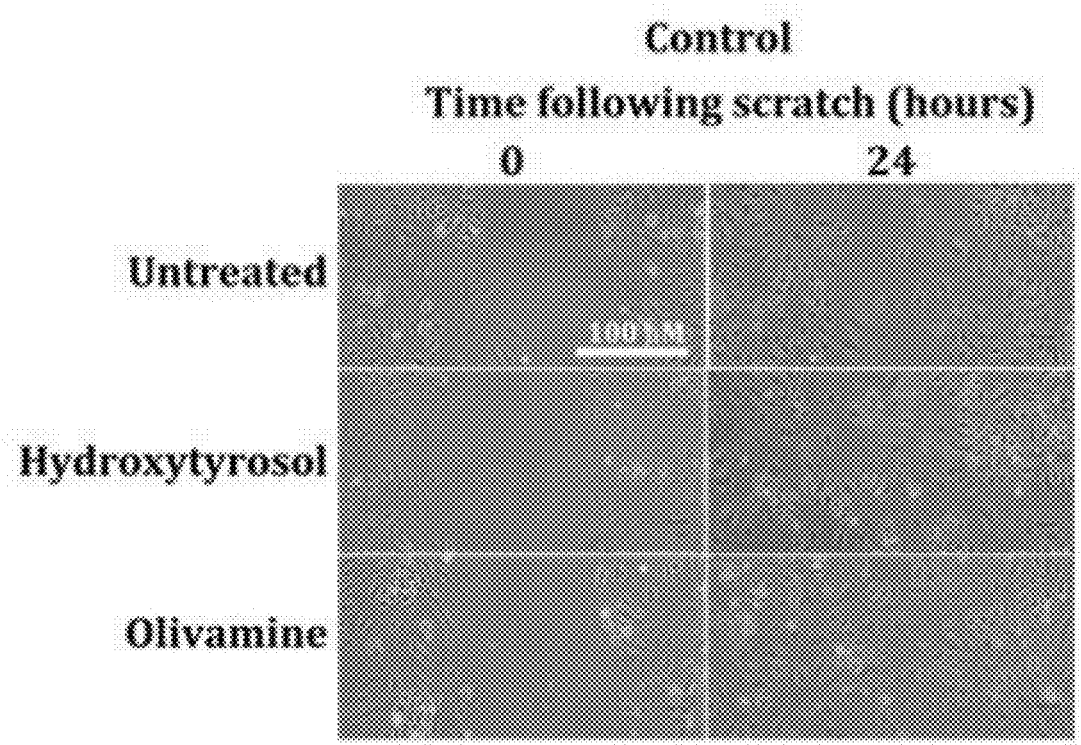
FIG. 7A shows images of various wounds at zero hours and 24 hours post-wound.
Figure 7B:
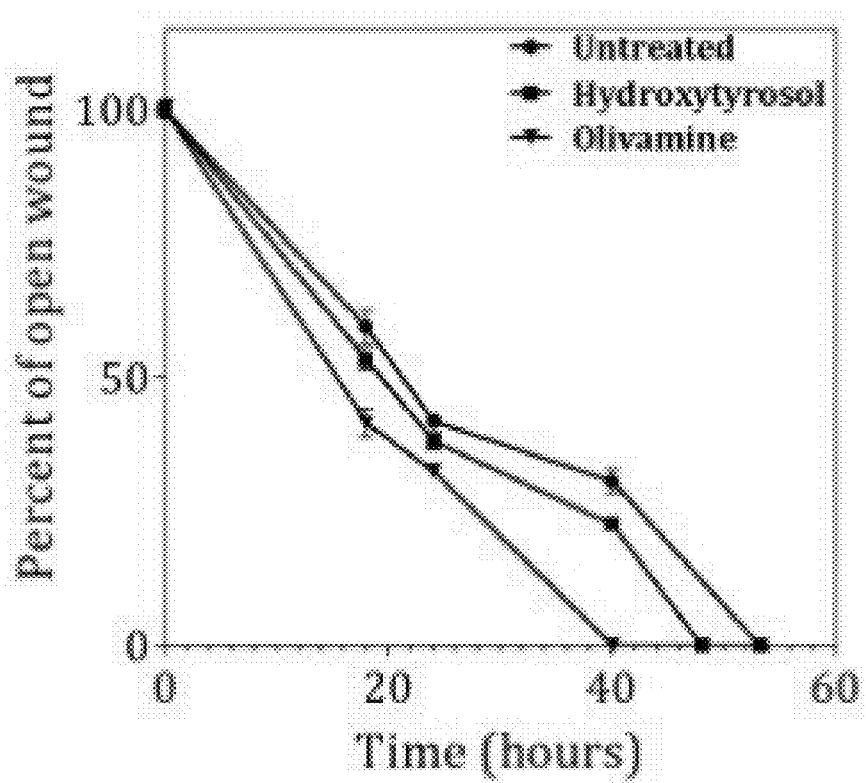
FIG. 7B shows graphically the healing (e.g. decrease in percentage of open wound) according to an untreated control, a wound administered hydroxytyrosol and a wound administered Olivamine according to an embodiment of the invention.
Figure 8A:
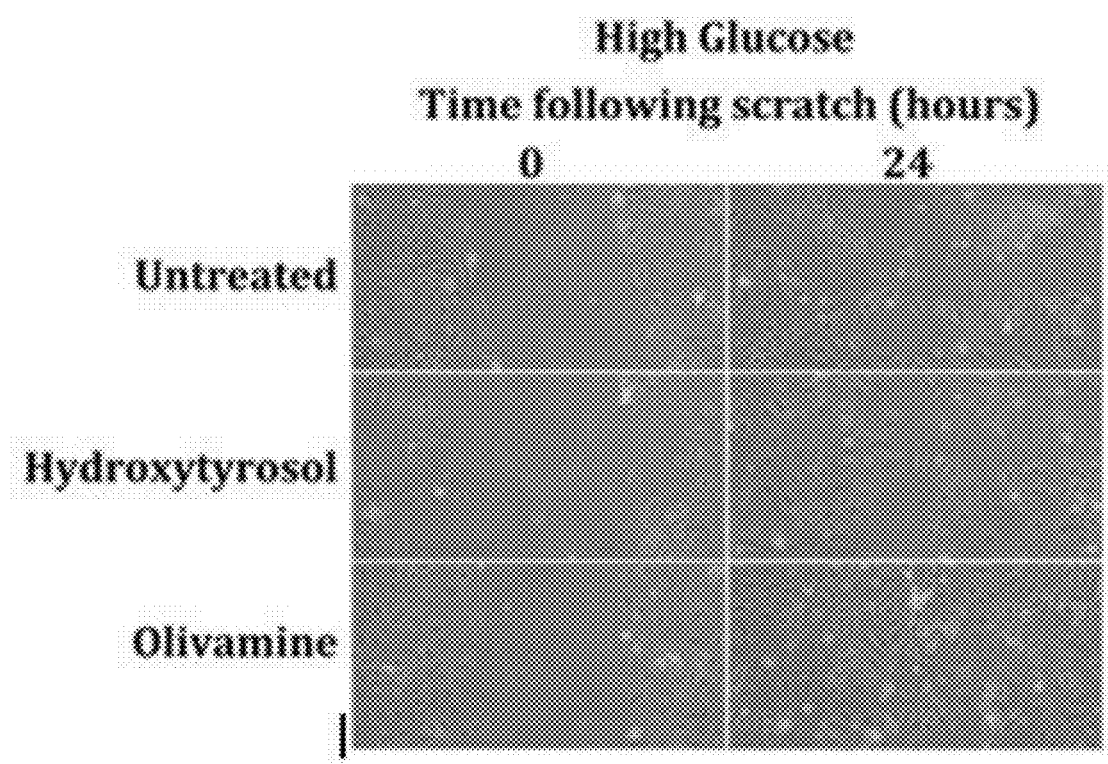
FIG. 8A shows images of various wounds at zero hours and 24 hours post-wound under high glucose conditions.
Figure 8B:
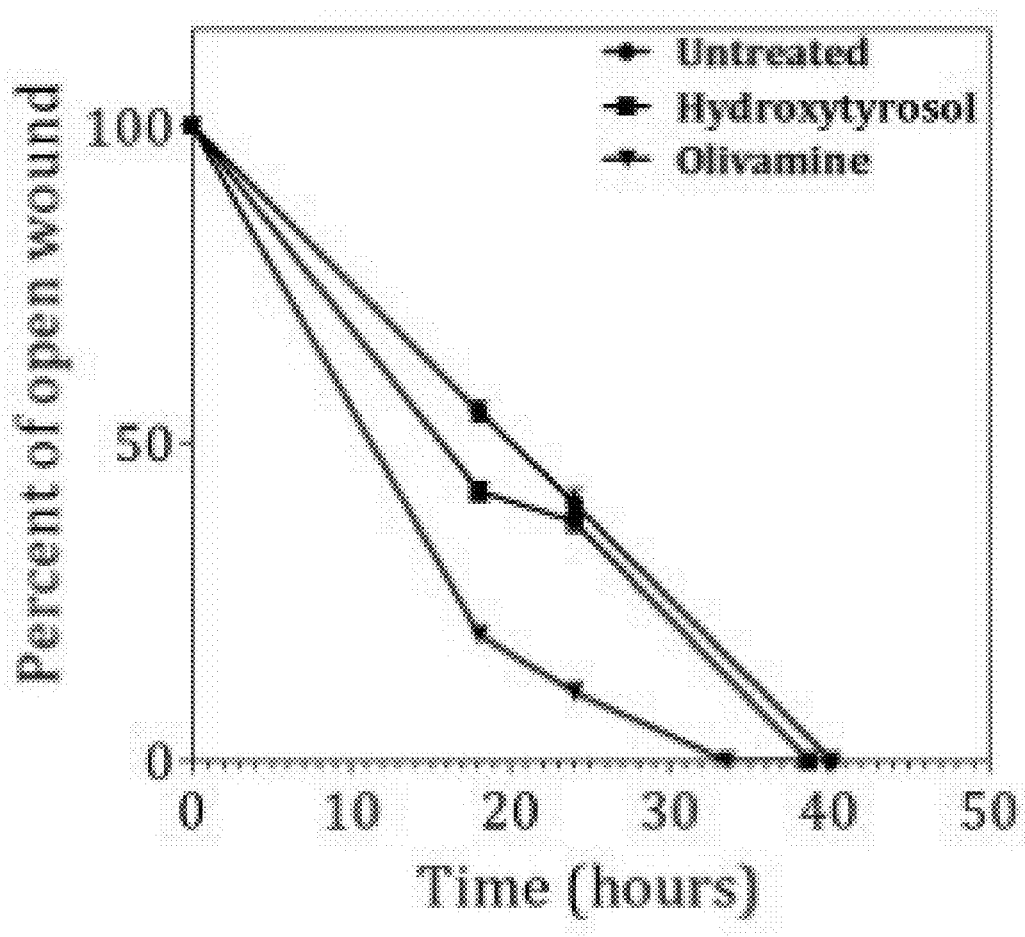
FIG. 8B shows graphically the healing (e.g. decrease in percentage of open wound) according to an untreated control, a wound administered hydroxytyrosol and a wound administered Olivamine according to an embodiment of the invention.
Figure 9A:
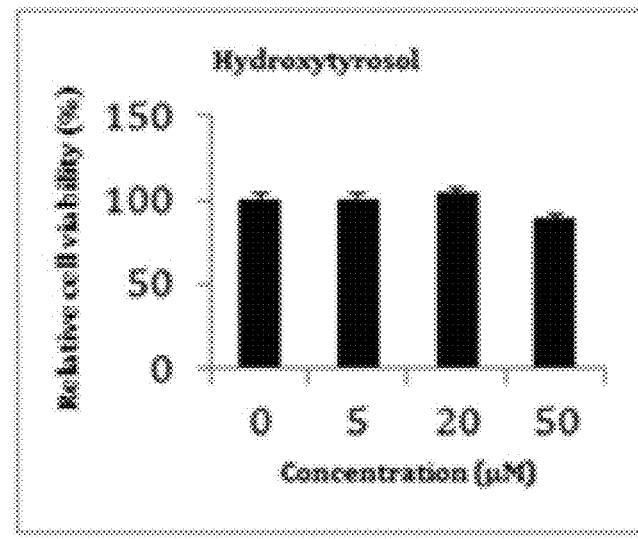
FIGS. 9A-9F show graphs of the tested effects of the individual components of the hydroxytyrosol and oleuropein compositions on the growth of a vascularized endothelial cell line according to embodiments of the invention.
Figure 9B:
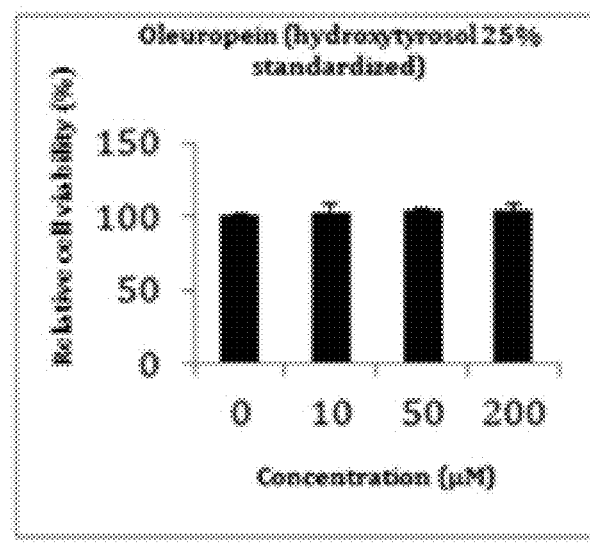
Figure 9C:
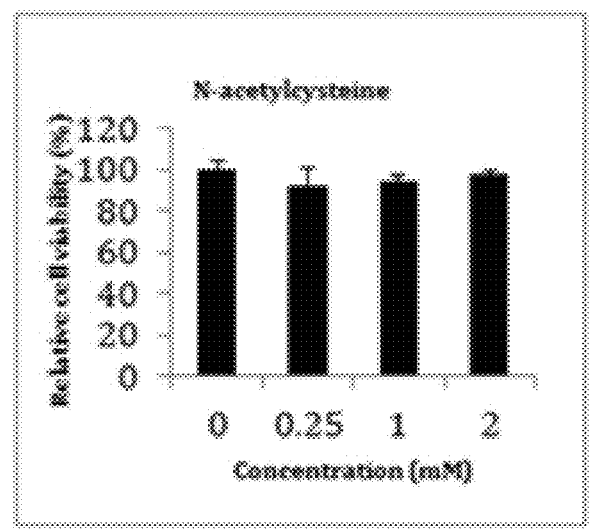
Figure 9D:
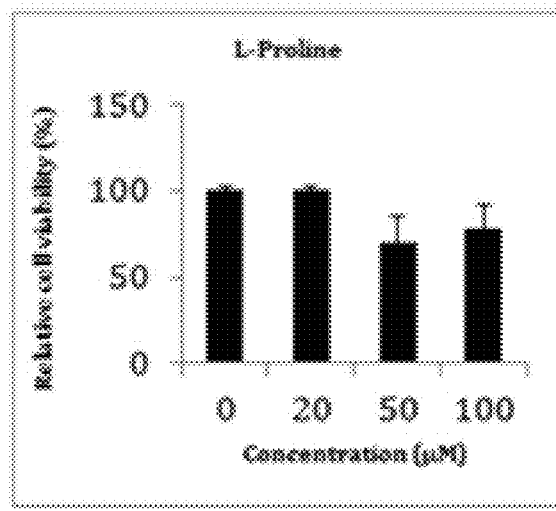
Figure 9E:
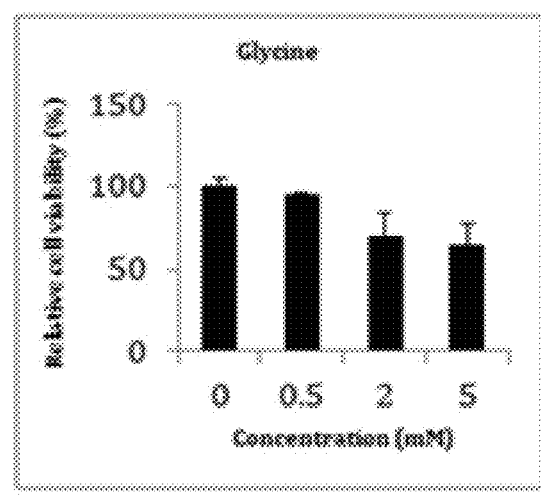
Figure 9F:
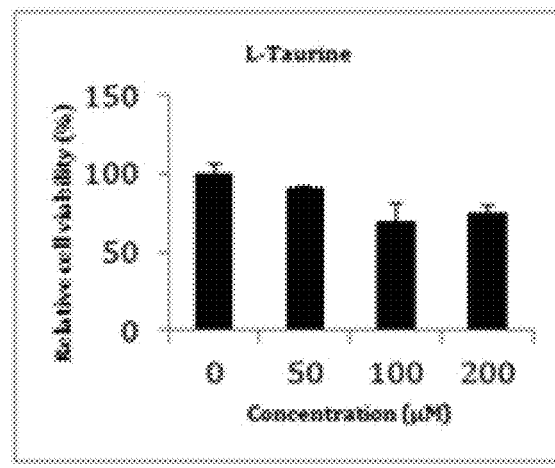

Images were taken at intervals and the wound gap was quantified over time using Image analysis software. For example, as shown in FIG. 6A, an initial image was taken at the time of injury (i.e. scratch) and the distance measured (as shown 734 microns); thereafter images are taken over incremental time periods (as shown in FIG. 6B the distance measured at 24 hours was 309 microns). The distances measured are depicted in the Figures by the horizontal solid lines indicating the distance between the gaps of the wound. 100 measurements were taken per image and a mean gap distance was determined. As shown in FIGS. 7-8 the initial wound and 24 hour measurement are shown by the images, under both control (FIG. 7A) and high glucose (FIG. 8A). In addition the reduction in percentage of open wound is further shown graphically for the control (FIG. 7B) and high glucose (FIG. 8B) conditions. The time for 50% of the wound to heal was quantified as well as the percentage of improvement compared to untreated cells.

The time for 50% of the wound to heal for the various treated tissues is shown in Table 2.

TABLE 2

| Treatment | | SEM |
|---|---|---|
| | Time for 50% wound to heal (hours) | |
| Untreated | 21.9 | 3.0 |
| Hydroxytyrosol | 19.7 | 2.1 |
| Olivamine | 15.3 | 3.2 |
| | High Glucose | |
| Untreated | 21.0 | 2.1 |
| Hydroxytyrosol | 15.2 | 2.0 |
| Olivamine | 8.6 | 1.0 |
| | Healing Improvement (%) | |
| Hydroxytyrosol | 10 | 2.1 |
| Olivamine | 30 | 2.7 |
| | High Glucose | |
| Hydroxytyrosol | 30 | 2.0 |
| Olivamine | 60 | 0.9 |

The results indicate that Olivamine improves cell migration by at least 60% in human umbilical vein endothelial cells following treatment with high glucose (i.e. toxic environments). This represents a significant improvement over the wound healing under the control/untreated (i.e. non-toxic environments) wherein a 30% improvement was observed. Beneficially, the use of Olivamine under the high glucose conditions resulted in a decrease in healing time (time for 50% wound healing) from 15.3 hours to 8.6 hours. These results are still more significant in comparing the untreated HUVEC cells which had a 50% wound healing at 21.9 hours (and still 21 hours under the high glucose conditions).

According to the invention, the use of Olivamine® compositions (20 µM hydroxytyrosol, 80 µM oleuropein, 2 mM N-acetylcysteine, 50 µM L-proline, 2 mM glycine and 100 µM taurine) provide a significant improvement in wound healing using HUVEC cells, and provide an even further improvement in toxic wound environments.

Example 3

The precise ranges of each of the components utilized within the hydroxytyrosol and oleuropein-containing compositions were evaluated (six ingredients in relation to one another). FIGS. 9A-F illustrate the tested effects of the individual components of the claimed compositions on the growth of a vascularized endothelial cell line (e.g. cells of the stomach lining). Scientific analysis was carried out using a cell culture assay to determine relative cell viability for each ingredient. Four initial concentrations were selected for initial concentrations (see Table 3) with a negative control. Individually the ingredients showed little (see 9B and 9C) to moderate (see 9A, 9D, 9E, 9F) impact on cellular growth.

TABLE 3

Initial Concentrations Tested

| Compound | | | | |
|---|---|---|---|---|
| Hydroxytyrosol ($\mu M$) | 0 | 5 | 20 | 50 |
| Oleuropein (hydroxytyrosol 25% standardized) ($\mu M$) | 0 | 10 | 50 | 200 |
| N-acetyl-cysteine (mM) | 0 | 0.25 | 1 | 2 |
| L-Proline ($\mu M$) | 0 | 20 | 50 | 100 |
| Glycine (mM) | 0 | 0.5 | 2 | 5 |
| L-Taurine ($\mu M$) | 0 | 50 | 100 | 200 |

Figure 10A:
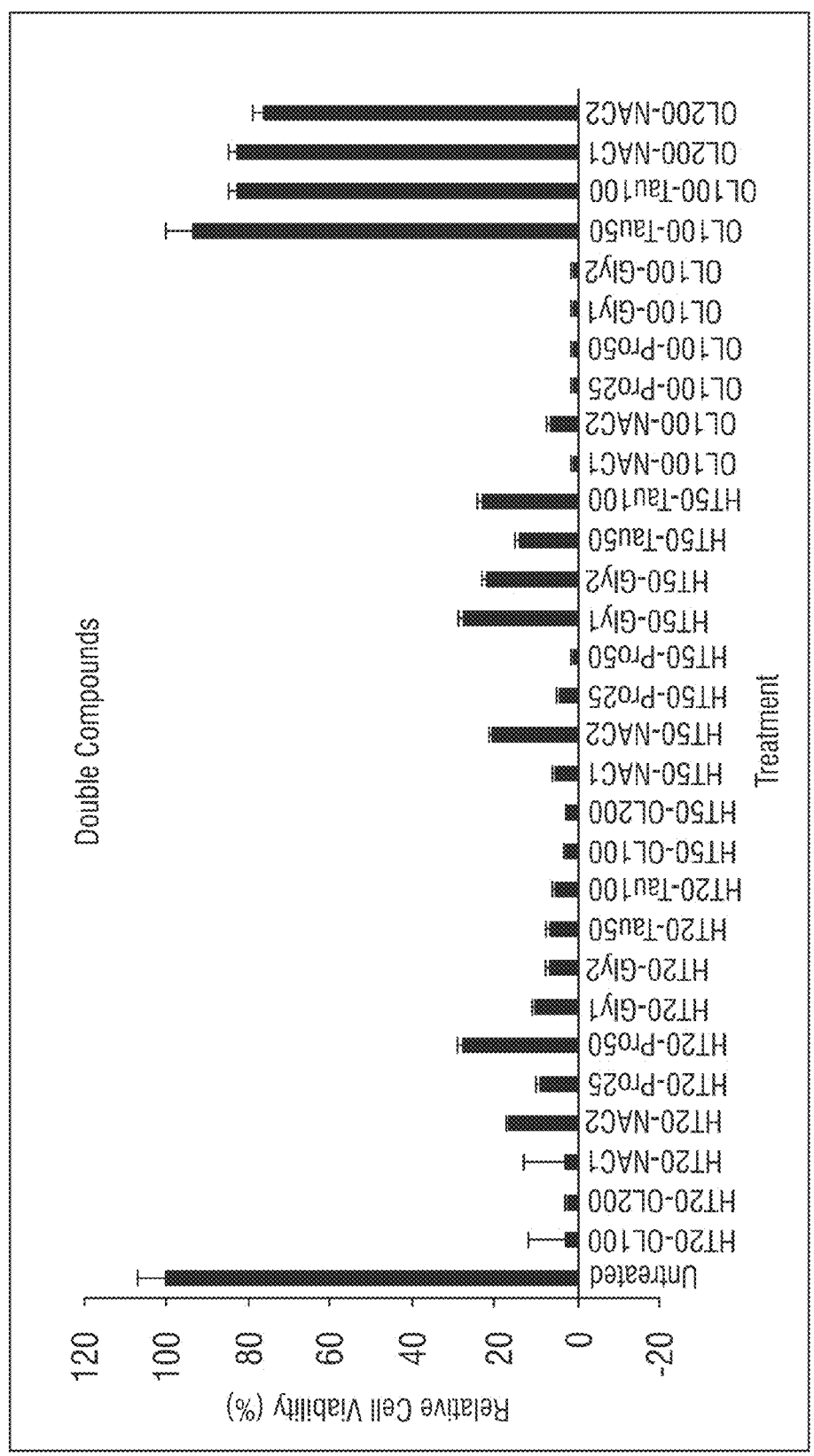
FIGS. 10A-10B show graphs of the tested effects of double component combinations of the hydroxytyrosol and oleuropein compositions on the growth of vascularized endothelial cell line according to embodiments of the invention.
Figure 10B:
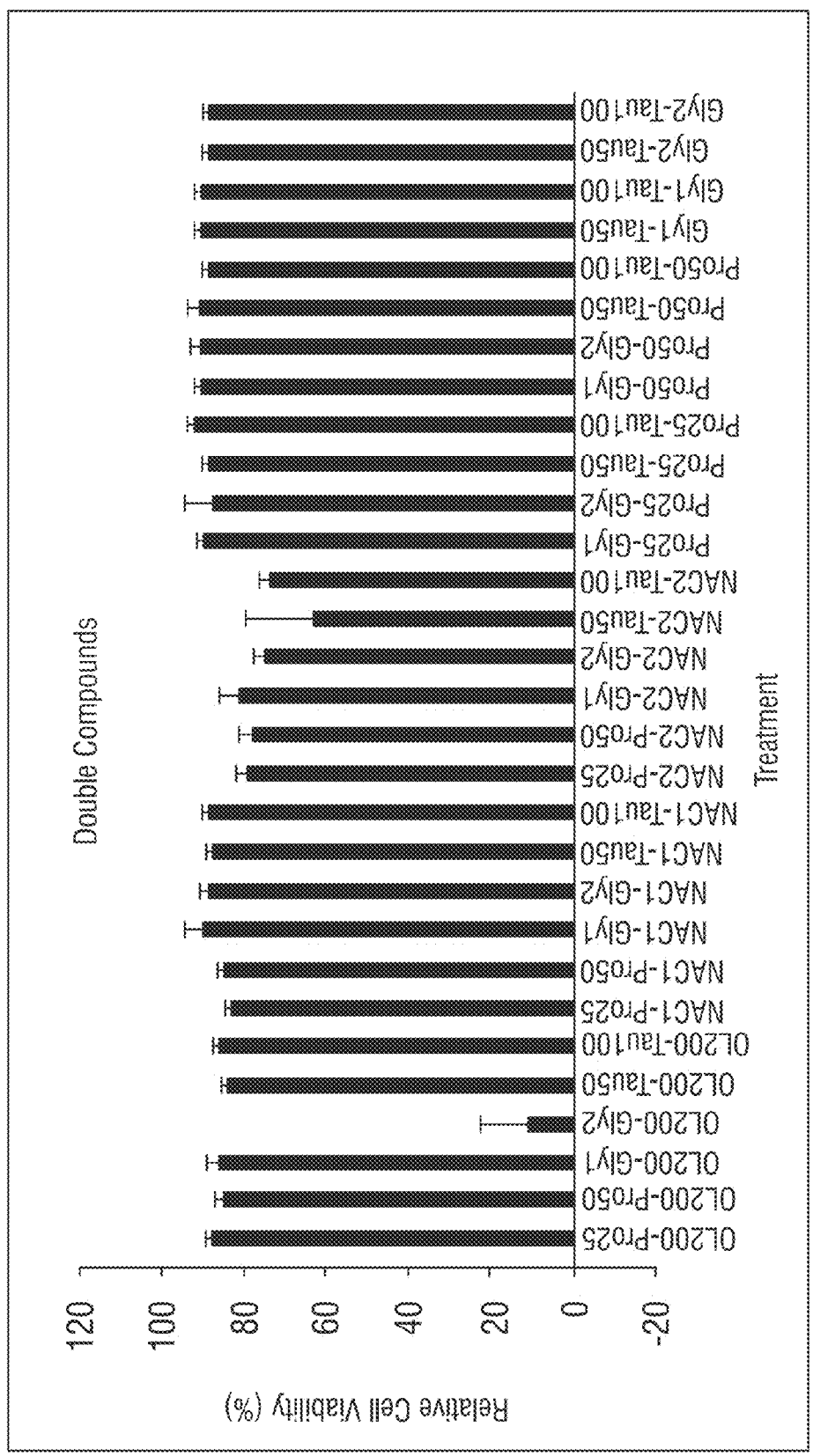

To calculate the needed ratios for the claimed compositions, a combination dosage study was conducted using the same testing method as described above on every two-ingredient combinations for the six ingredients (see FIG. 10). Ingredient concentrations were determined using the top two preforming concentrations from the initial study (shown in FIGS. 9A-F) with adjustments for oleuropein (hydroxytyrosol 25% standardized), glycine and L-Proline (see Table 4). The second combination and dosage study determined ingredient interactions and dosages for the final concentrations to be used for remaining test sets (see Table 5).

TABLE 4

Concentrations for Second Test Set

| Compounds | | |
|---|---|---|
| Hydroxytyrosol ($\mu M$) | 20 | 50 |
| Oleuropein (hydroxytyrosol 25% standardized) ($\mu M$) | 100 | 200 |
| N-acetyl-cysteine (mM) | 1 | 2 |
| L-Proline ($\mu M$) | 25 | 50 |
| Glycine (mM) | 1 | 2 |
| L-Taurine ($\mu M$) | 50 | 100 |

Figure 11:
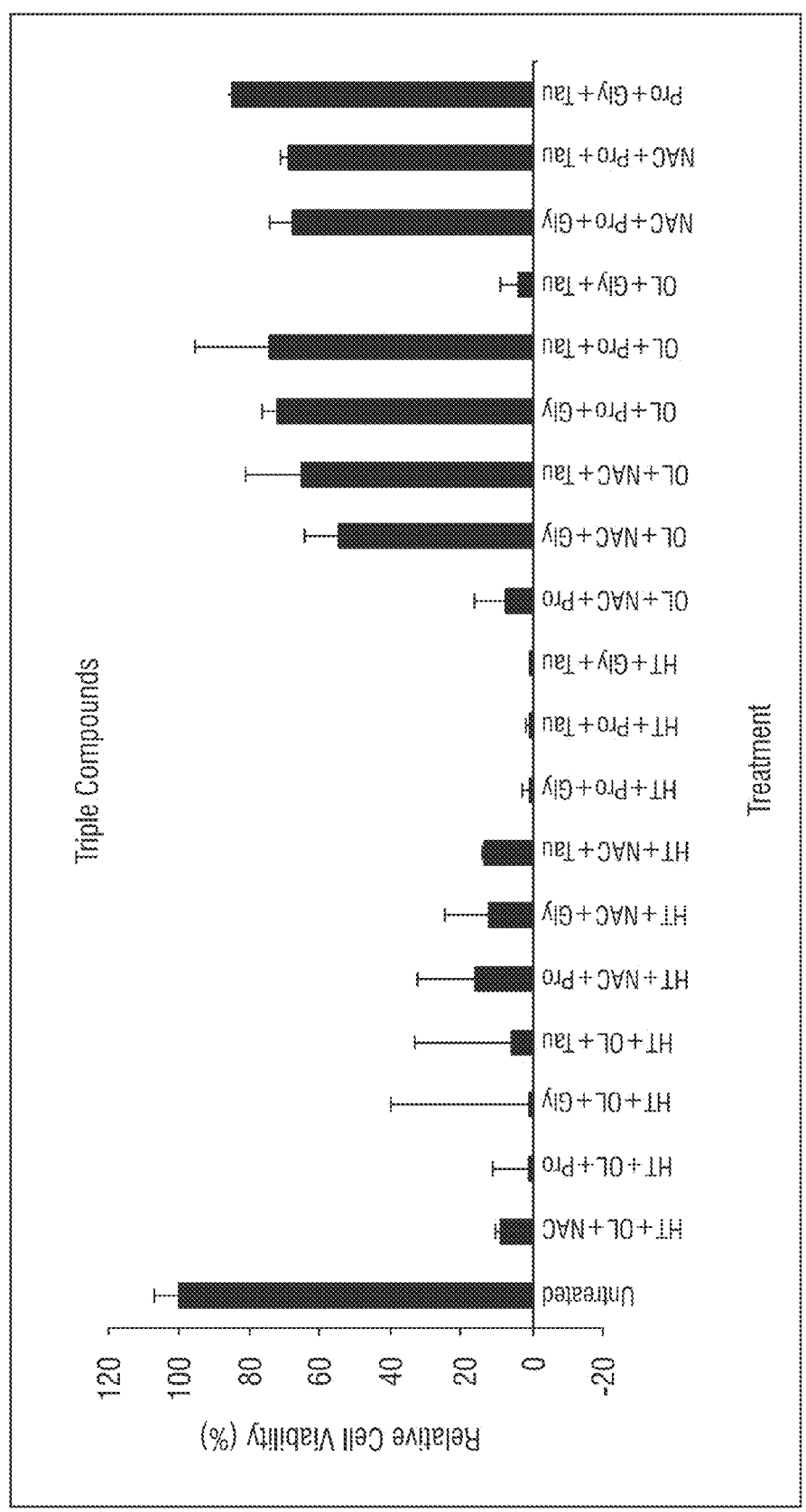
FIG. 11 shows a graph of the tested effects of triple component combinations of the hydroxytyrosol and oleuropein compositions on the growth of a vascularized endothelial cell line according to embodiments of the invention.

Further component amount/ratio evaluation was continued by using every unique triple ingredient combination for the six ingredients. Concentrations used were determined by the second test set (see Table 5). Ingredient synergy was observed for some combinations and no negative ingredient interactions for synergy were observed (see FIG. 11). The importance of hydroxytyrosol to the present art was determined.

TABLE 5

Concentrations for Third Test Set

| Triple | |
|---|---|
| Hydroxytyrosol ($\mu M$) | 50 |
| Oleuropein (hydroxytyrosol 25% standardized) ($\mu M$) | 200 |
| N-acetyl-cysteine (mM) | 2 |
| L-Proline ($\mu M$) | 50 |
| Glycine (mM) | 2 |
| L-Taurine ($\mu M$) | 100 |

Figure 12:
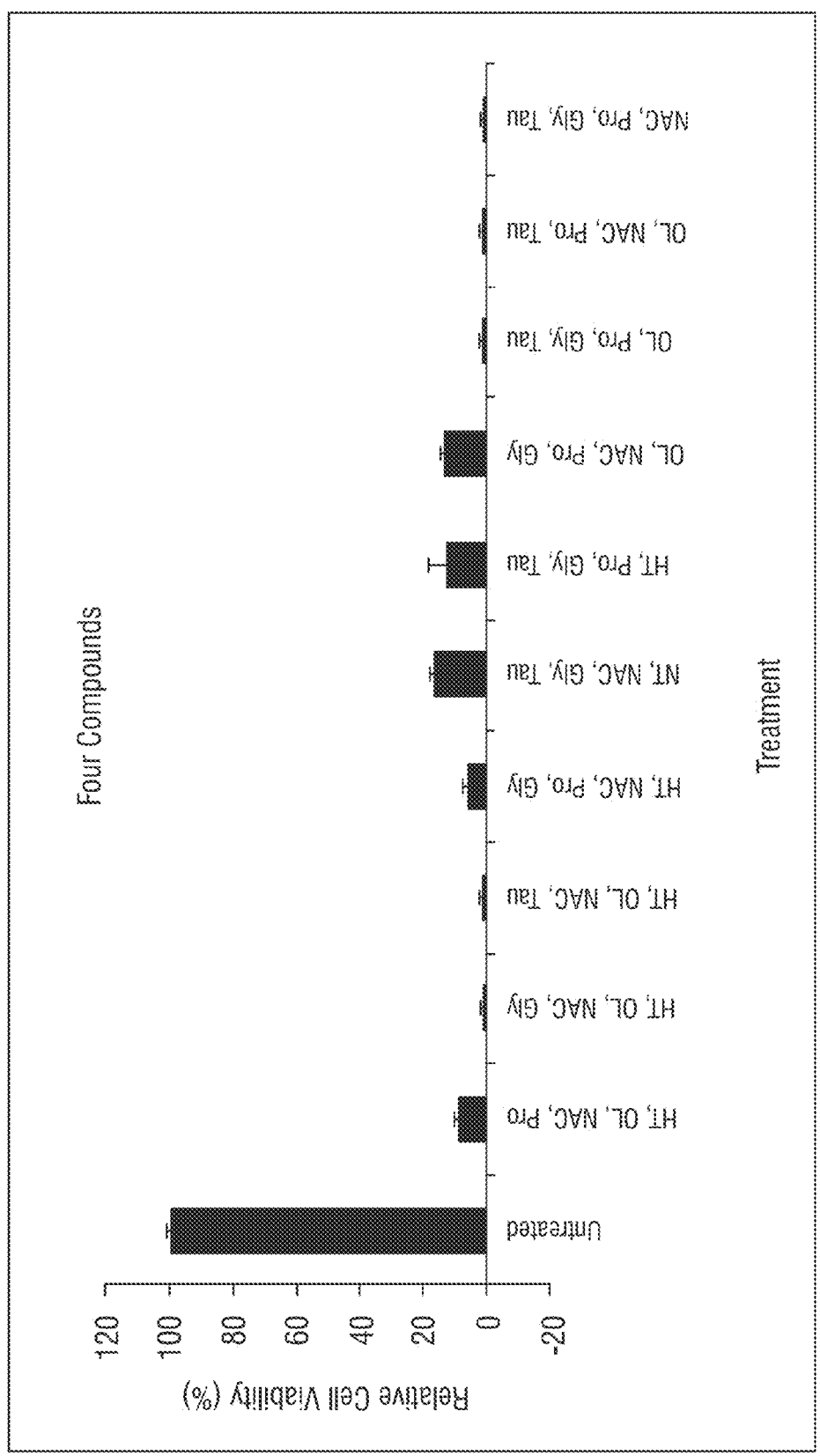
FIG. 12 shows a graph of the tested effects of four-way component combinations of the hydroxytyrosol and oleuropein compositions on the growth of a vascularized endothelial cell line according to embodiments of the invention.

The four compound combinations were further performed following the same procedure of the previous test sets, with ingredient synergy becoming apparent and no negative ingredient interactions observed (see Table 6). The importance of L-proline to the present art was determined (see FIG. 12).

TABLE 6

Combinations and Concentrations of Four Compound Combination Test

| Four Compounds | | | | |
|---|---|---|---|---|
| HT + Oleuropein + N-acetyl-cysteine + Proline | 50 ($\mu M$) | 200 ($\mu M$) | 2 (mM) | 50 ($\mu M$) |
| HT + Oleuropein + N-acetyl-cysteine + Glycine | 50 ($\mu M$) | 200 ($\mu M$) | 2 (mM) | 2 (mM) |
| HT + Oleuropein + N-acetyl-cysteine + Taurine | 50 ($\mu M$) | 200 ($\mu M$) | 2 (mM) | 100 ($\mu M$) |
| HT + N-acetyl-cysteine + Proline + Taurine | 50 ($\mu M$) | 2 (mM) | 50 ($\mu M$) | 100 ($\mu M$) |
| HT + Proline + Glycine + Taurine | 50 ($\mu M$) | 50 ($\mu M$) | 2 (mM) | 100 ($\mu M$) |
| Oleuropein + N-acetyl-cysteine + Proline + Glycine | 200 ($\mu M$) | 2 (mM) | 50 ($\mu M$) | 2 (mM) |
| Oleuropein + Proline + Glycine + Taurine | 200 ($\mu M$) | 50 ($\mu M$) | 2 (mM) | 100 ($\mu M$) |
| HT + N-acetyl-cysteine + Glycine + Taurine | 50 ($\mu M$) | 2 (mM) | 2 (mM) | 100 ($\mu M$) |
| Oleuropein + N-acetyl-cysteine + Proline + Taurine | 200 ($\mu M$) | 2 (mM) | 50 ($\mu M$) | 100 ($\mu M$) |
| N-acetyl-cysteine + Proline + Glycine + Taurine | 2 (mM) | 50 ($\mu M$) | 2 (mM) | 100 ($\mu M$) |

A fifth set of experiments following the previously described test procedure was used to determine the importance of six ingredients for the claimed compositions, excluding hydroxytyrosol and L-proline (established above) (see Table 7). The importance of the oleuropein (hydroxytyrosol 25% standardized)-hydroxytyrosol ingredient interaction to the synergy of the present art was observed (see FIG. 12).

TABLE 7

Combinations and Concentrations of Five Compound Combination Test

Five Compounds

| | | | | | |
|---|---|---|---|---|---|
| HT + Oleuropein + N-acetyl-cysteine + L-Proline + Glycine | 50 (μM) | 200 (μM) | 2 (mM) | 50 (μM) | 2 (mM) |
| HT + Oleuropein + N-acetyl-cysteine + L-Proline + L-Taurine | 50 (μM) | 200 (μM) | 2 (mM) | 50 (μM) | 100 (μM) |
| HT + N-acetyl-cysteine + L-Proline + Glycine + L-Taurine | 50 (μM) | 2 (mM) | 50 (μM) | 2 (mM) | 100 (μM) |
| HT + Oleuropein + L-Proline + Glycine + L-Taurine | 50 (μM) | 200 (μM) | 50 (μM) | 2 (mM) | 100 (μM) |

Figure 13:
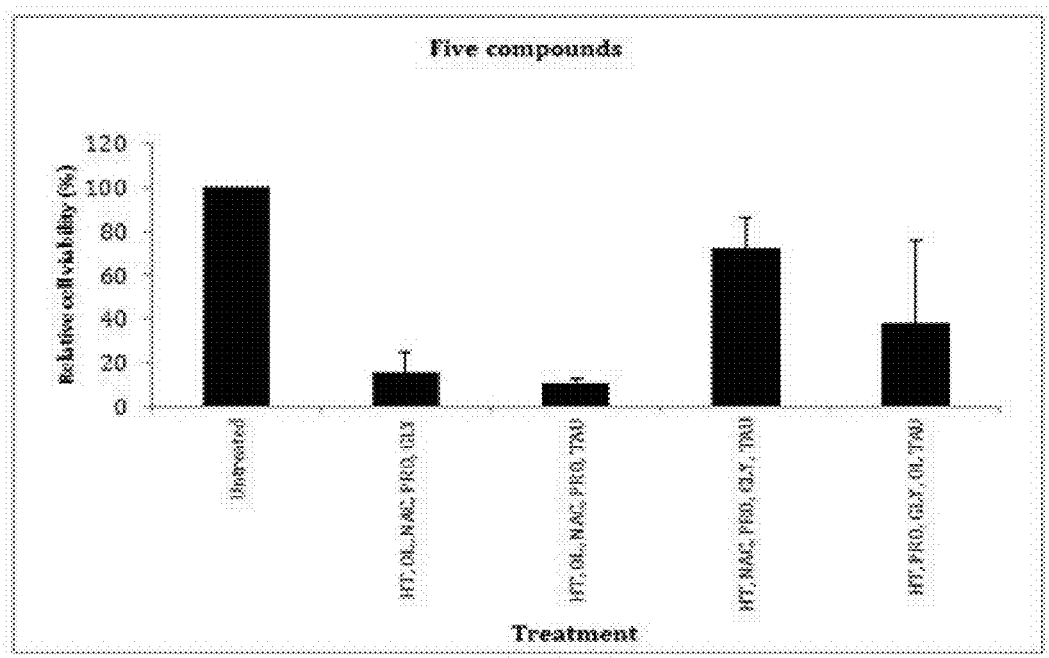
FIG. 13 shows a graph of the tested effects of five-way component combinations of the hydroxytyrosol and oleuropein compositions on the growth of a vascularized endothelial cell line according to embodiments of the invention.
Figure 14:
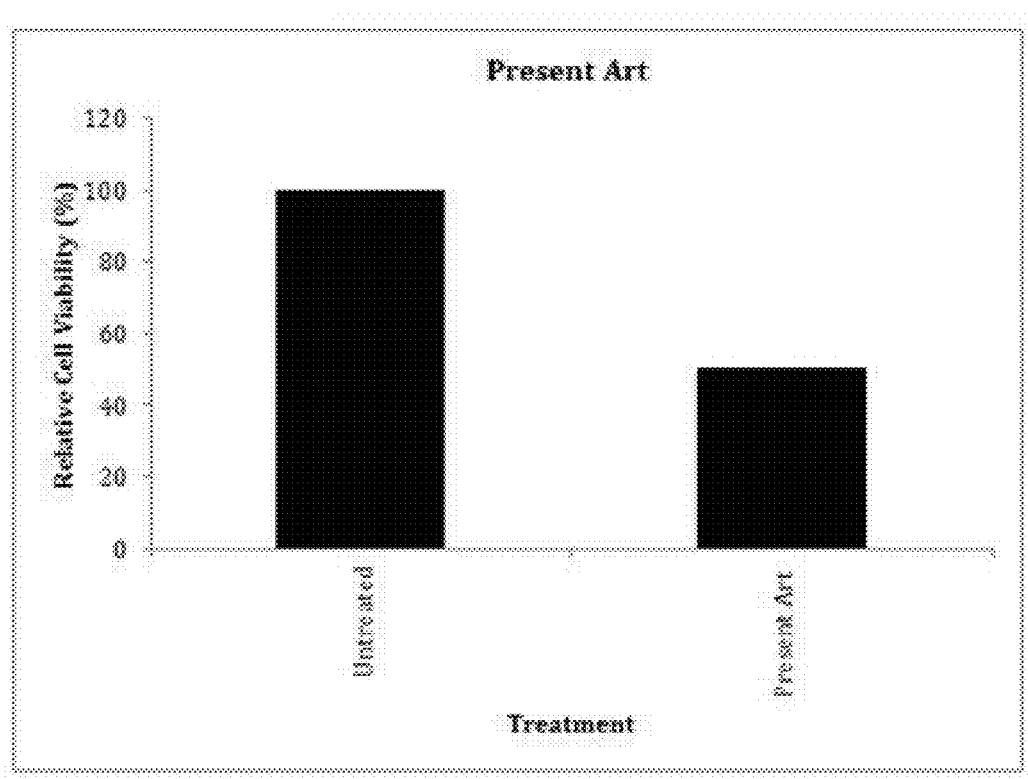
FIG. 14 shows a graph of the compositions according to the invention on the relative cell viability of a vascularized endothelial cell line according to embodiments of the invention.

Three compound compositions were generated with the previously outlined component ingredient synergy (see Table 8). Radiation protection studies and relative cell viability in vitro testing was used to establish the final claimed compositions with established synergy in its impact of the cell growth of vascularized endothelial cells (see FIG. 13).

TABLE 8

Optimized Formulation 1 for Testing

| Compound | Formulation 1 Concentration/Percentage (μM)/(%) | Formulation 2 Concentration/Percentage (μM)/(%) | Formulation 3 Concentration/Percentage (μM)/(%) |
|---|---|---|---|
| Hydroxytyrosol | 200 (1.26) | 100 (0.7) | 200 (0.9) |
| Oleuropein (hydroxytyrosol 25% standardized) | 800 (17.7) | 400 (9.78) | 800 (12.66) |
| N-acetyl-cysteine | 8000 (53.45) | 8000 (59.05) | 8000 (38.21) |
| L-Proline | 200 (0.94) | 200 (1.04) | 400 (1.35) |
| Glycine | 8000 (24.59) | 8000 (27.16) | 20000 (43.93) |
| L-Taurine | 400 (2.05) | 400 (2.26) | 800 (2.93) |

Figure 15:
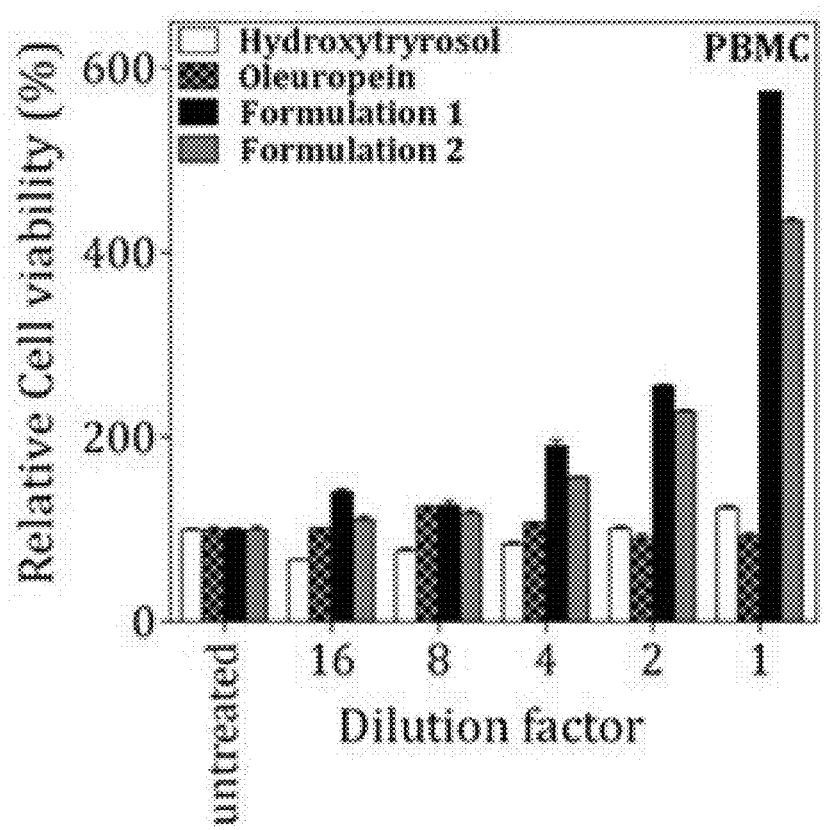
FIG. 15 shows a graph of various tested formulations to show the impact on relative cell viability of a vascularized endothelial cell line according to embodiments of the invention.
Figure 16:
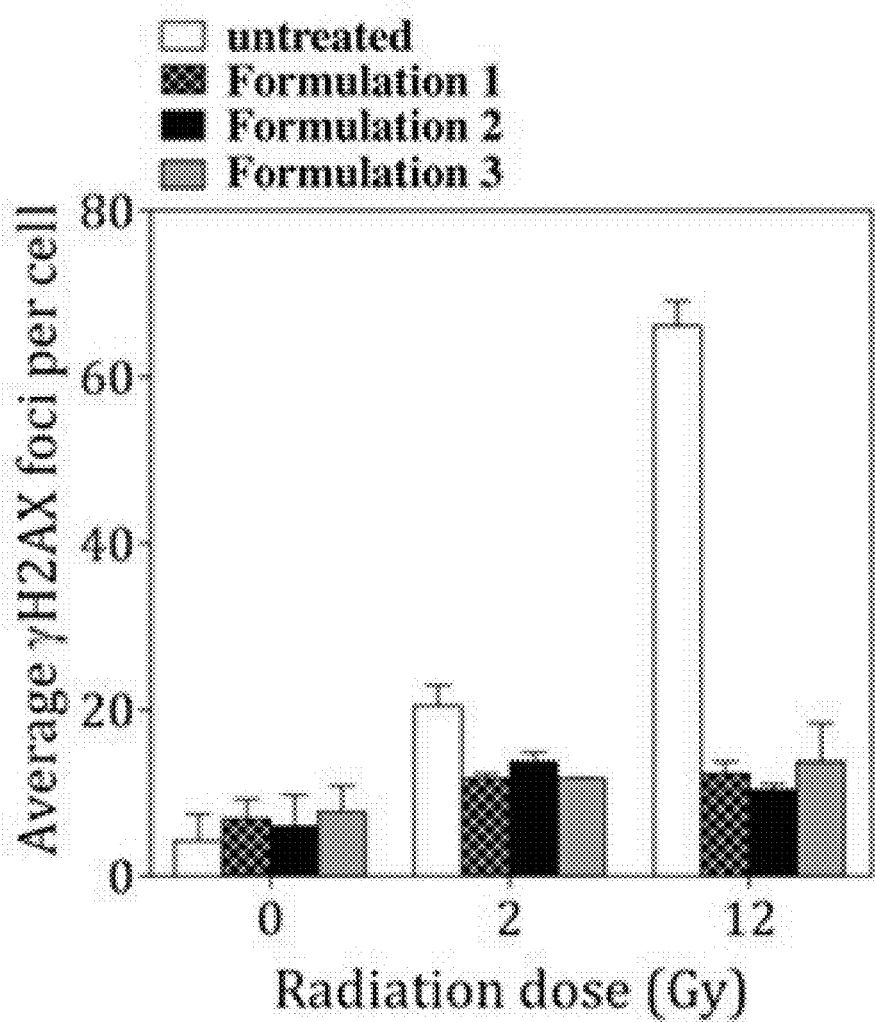
FIGS. 16-17 shows a graph of various tested formulations to show the impact on the average $\gamma$H2AX foci per cell according to embodiments of the invention for wound healing.

The three formulations were analyzed for compound synergy and cell proliferative properties of healthy cells. The first test set was a dilution test conducted on compounds 1 and 2, and the individual ingredients hydroxytyrosol and oleuropein (hydroxytyrosol 25% standardized) and their impact on relative cell viability. Compound 1 showed a synergistic ability to promote the growth of healthy cells (see FIG. 15). The second test set conducted was a radiation protection study of healthy cells conducted on Formulations 1, 2, and 3 and the individual ingredients hydroxytyrosol and oleuropein (hydroxytyrosol 25% standardized). The average γH2AX foci per cell was used as a measure of radiation induced DNA damage in the cell. Formulation 1 showed the best ability to protect cells in doses of 2 Gy and showed moderately less protective effect in doses of 12 Gy as compared to Compound 2 (see FIG. 16).

Figure 17:
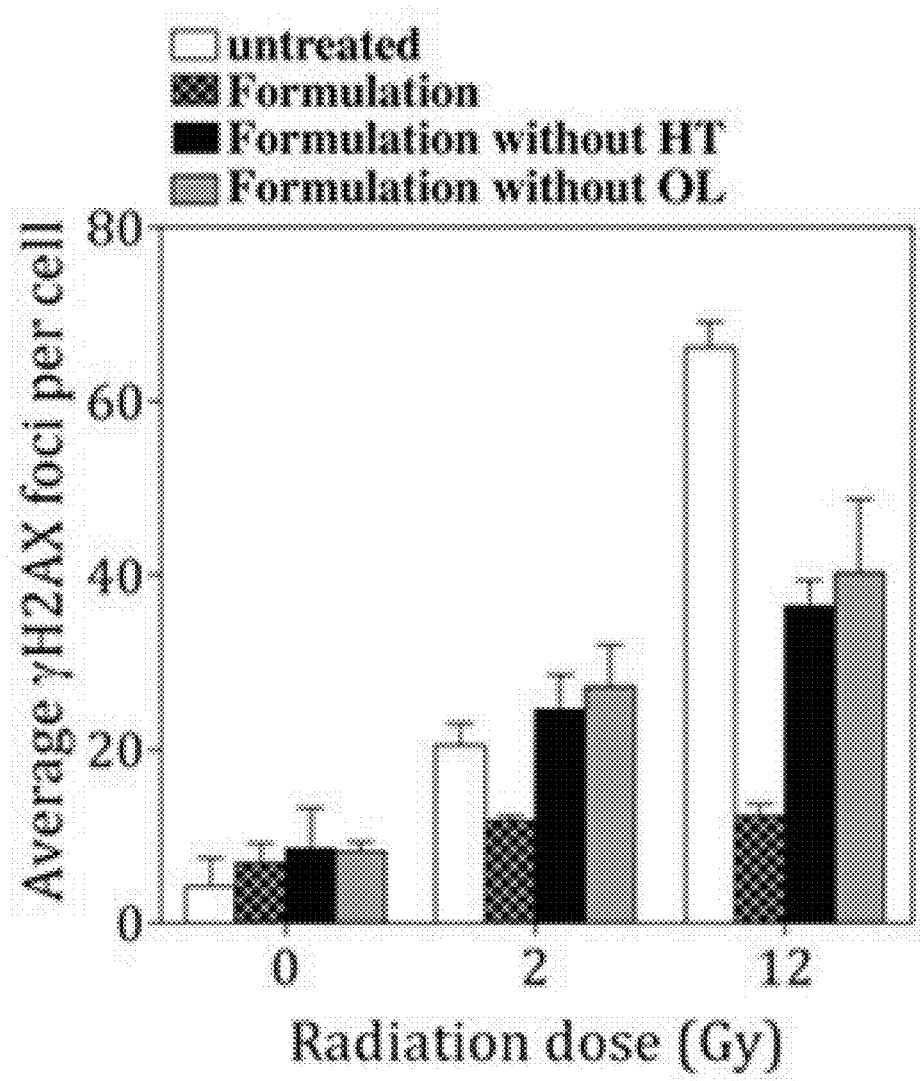
Figure 18:
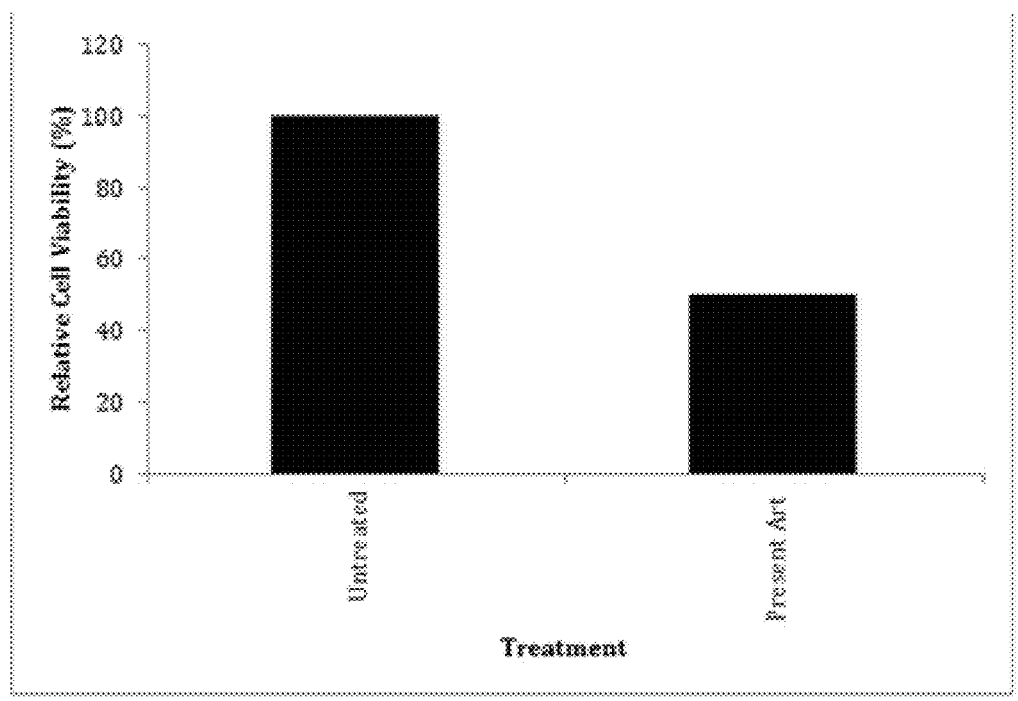
FIG. 18 shows a graph of the compositions according to the invention on the relative cell viability of a vascularized endothelial cell line according to embodiments of the invention.

Based on its synergistic abilities to promote healthy cell growth and to protect healthy cells from DNA damage when exposed to radiation Formulation 1 demonstrates the greatest cytoprotective effect for healthy cells (see Table 9). Compound synergy was determined using the same radiation protection study as described above, conducted on two formulation without the ingredients hydroxytyrosol and oleuropein (hydroxytyrosol 25% standardized) respectively in comparison to Formulation 1. Formulation 1 showed synergistic radiation protective effects as compared to the formulations without hydroxytyrosol and oleuropein (hydroxytyrosol 25% standardized) (see FIG. 17). Synergy was further confirmed with a relative cell viability assay using the same procedure as described for the previous tests. The formulation showed significant synergistic impact on the relative cell viability of vascularized endothelial cells (see FIG. 18).

TABLE 9

| Treatment | Time for 50% wound to heal (hours) | SD |
|---|---|---|
| Untreated | 26.01 | 0.71 |
| Present Art | 17.75 | 1.06 |
| Hydroxytyrosol | 19.25 | 1.84 |
| Oleuropein | 25.62 | 2.17 |
| N-acetylcysteine | 28.87 | 1.95 |
| L-proline | 23.24 | 1.53 |
| Glycine | 20.73 | 2.08 |
| L-Taurine | 22.5 | 1.83 |
| Present Art Without . . . | | |
| Hydroxytyrosol | 26.59 | 4.29 |
| Oleuropein | 31.25 | 3.66 |
| N-acetylcysteine | 56.99 | 6.68 |
| L-proline | 19.84 | 0.51 |
| Glycine | 28.58 | 0.66 |
| L-Taurine | 30.28 | 1.81 |

The various outlined demonstrations of the criticality of the claimed amounts/ratios of the compositions according to the present invention show the unexpected results obtained from the strong synergistic effect obtained by the combinations within the formulation.

The inventions being thus described, it will be obvious that the same may be varied in many ways. Such variations are not to be regarded as a departure from the spirit and scope of the inventions and all such modifications are intended to be included within the scope of the following claims.

What is claimed:

1. A method for accelerating wound closure to improve wound healing comprising:
    administering or transplanting to a subject in need of wound healing a composition comprising an effective amount of hydroxytyrosol and oleuropein and an effective amount of cells derived from umbilical cord blood, wherein the administration of the composition reduces the time required for healing of the wound by at least about 30% in comparison to a composition treated with the cells derived from umbilical cord blood alone.

2. The method according to claim 1, wherein the cells derived from umbilical cord blood are umbilical cord stem cells, or a cultured medium conditioned by said umbilical cord stem cells.

3. The method according to claim 1, wherein the cells derived from umbilical cord blood are transplanted to a wound in need of healing.

4. The method according to claim 1, wherein the ratio of hydroxytyrosol to oleuropein is from about 1:1 to about 10:1.

5. The method according to claim 1, wherein the composition further comprises N-acetyl cysteine, glycine, taurine and L-proline.

6. The method according to claim 1, wherein the weight ratio of N-acetyl cysteine to hydroxytyrosol is between 1:1 and 50:1, wherein the weight ratio of glycine to hydroxytyrosol is between 1:1 and 50:1, wherein the ratio of taurine to hydroxytyrosol is between 1:1 and 50:1, and wherein the weight ratio of L-proline to hydroxytyrosol is between 1:1 and 20:1.

7. The method according to claim 1, wherein the composition is topically applied.

8. The method according to claim 1, wherein the wound is a skin wound characterized by a partial or total loss of skin and is surrounded by a peri-wound region.

9. The method according to claim 8, wherein the composition is applied to the peri-wound region and has a concentration of hydroxytyrosol less than 225 µM and a concentration of oleuropein less than 900 µM.

10. The method according to claim 8, wherein the composition is applied to the wound region and has a concentration of hydroxytyrosol less than 15 µM and a concentration of oleuropein less than 60 µM.

11. A method for promoting cellular migration to improve wound healing comprising:
topically administering or transplanting to a subject in need of wound healing a composition comprising hydroxytyrosol and oleuropein and cells derived from umbilical cord blood; and
reducing the time required for wound healing at least 50% of a wound, as measured by cellular migration to close a wound, to below at least 12 hours.

12. The method according to claim 11, wherein the wound healing further comprises promoting keratinocyte and fibroblast proliferation and/or neovascularization.

13. The method according to claim 11, wherein the cells derived from umbilical cord blood are umbilical cord stem cells, or a cultured medium conditioned by said umbilical cord stem cells.

14. The method according to claim 11, wherein the ratio of hydroxytyrosol to oleuropein is from about 1:1 to about 10:1.

15. The method according to claim 11, wherein the composition further comprises N-acetyl cysteine, glycine, taurine and L-proline.

16. The method according to claim 15, wherein the weight ratio of N-acetyl cysteine to hydroxytyrosol is between 1:1 and 50:1, wherein the weight ratio of glycine to hydroxytyrosol is between 1:1 and 50:1, wherein the ratio of taurine to hydroxytyrosol is between 1:1 and 50:1, and wherein the weight ratio of L-proline to hydroxytyrosol is between 1:1 and 20:1.

17. The method according to claim 11, wherein weight ratio N-acetyl cysteine to hydroxytyrosol is between 10:1 and 30:1, the weight ratio glycine to hydroxytyrosol is between 30:1 and 40:1, the weight ratio of taurine to hydroxytyrosol is between 20:1 and 50:1, and wherein the weight ratio of L-proline to hydroxytyrosol is between 1:1 and 10:1.

18. The method according to claim 11, wherein the time required for healing at least 50% of a wound is reduced to below at least 8 hours.

* * * * *